US012673003B2

(12) United States Patent
Tagami

(10) Patent No.: US 12,673,003 B2
(45) Date of Patent: Jul. 7, 2026

(54) BLOOD VESSEL TRAINING DEVICE, METHOD, BLOOD VESSEL TRAINING SYSTEM

(71) Applicant: NALUX Co., Ltd., Osaka (JP)

(72) Inventor: Katsutoshi Tagami, Asaka (JP)

(73) Assignee: NALUX Co., Ltd, Osaka (JP)

( * ) Notice: Subject to any disclaimer, the term of this patent is extended or adjusted under 35 U.S.C. 154(b) by 409 days.

(21) Appl. No.: 18/556,217

(22) PCT Filed: Jan. 26, 2022

(86) PCT No.: PCT/JP2022/002827
§ 371 (c)(1),
(2) Date: Oct. 19, 2023

(87) PCT Pub. No.: WO2022/224518
PCT Pub. Date: Oct. 27, 2022

(65) Prior Publication Data
US 2024/0261174 A1 Aug. 8, 2024

(30) Foreign Application Priority Data

Apr. 20, 2021 (JP) ................................. 2021-070849

(51) Int. Cl.
*A61B 5/02* (2006.01)
*A61B 5/021* (2006.01)
(Continued)

(52) U.S. Cl.
CPC ....... *A61H 9/0092* (2013.01); *A61B 5/02007* (2013.01); *A61B 5/02116* (2013.01);
(Continued)

(58) Field of Classification Search
None
See application file for complete search history.

(56) References Cited

U.S. PATENT DOCUMENTS 6,149,618 A 11/2000 Sato
9,775,619 B2 10/2017 Sato

FOREIGN PATENT DOCUMENTS

JP 2670421 B2 10/1997
JP 2008099842 A 5/2008
(Continued)

OTHER PUBLICATIONS

International Search Report and Written Opinion of the International Searching Authority issued Apr. 12, 2022 in International Application No. PCT/JP2022/002827, and English translation of the International Search Report.

*Primary Examiner* — Levon J Shahinian
(74) *Attorney, Agent, or Firm* — Plumsea Law Group, LLC

(57) ABSTRACT

Provided is a technology for grasping a degree of improvement in elasticity of a blood vessel before and after blood vessel training. A pressure applying belt including a gas bladder, which is similar to a cuff for measuring blood pressure, is used to execute the blood vessel training (blood flow restriction training). Pre-processing and post-processing are performed before and after treatment processing. In the pre-processing, a pre-maximum pulse wave amplitude, which is a pulse wave amplitude that became maximum, is identified. In the post-processing, a post-maximum pulse wave amplitude, which is a pulse wave amplitude that became maximum, is identified. After the post-processing is ended, a ratio between the pre-maximum pulse wave amplitude and the post-maximum pulse wave amplitude is obtained.

13 Claims, 11 Drawing Sheets

(51) Int. Cl.

| | | |
|---|---|---|
| *A61B 5/022* | (2006.01) | |
| *A61H 9/00* | (2006.01) | |
| *A63B 21/00* | (2006.01) | |
| *A63B 21/008* | (2006.01) | |
| *A63B 24/00* | (2006.01) | |

(52) U.S. Cl.

CPC ...... *A61B 5/02141* (2013.01); *A61B 5/02225* (2013.01); *A61B 5/02233* (2013.01); *A61H 9/0007* (2013.01); *A63B 21/0085* (2013.01); *A63B 21/4011* (2015.10); *A63B 21/4017* (2015.10); *A63B 24/0087* (2013.01); *A61H 2201/165* (2013.01); *A61H 2201/5005* (2013.01); *A61H 2201/5058* (2013.01); *A61H 2209/00* (2013.01); *A63B 2024/0093* (2013.01); *A63B 2208/05* (2013.01); *A63B 2209/10* (2013.01); *A63B 2230/062* (2013.01)

(56) References Cited

FOREIGN PATENT DOCUMENTS

| | | |
|---|---|---|
| JP | 5255722 B1 | 8/2013 |
| JP | 2014028109 A | 2/2014 |
| WO | 2017082274 A1 | 5/2017 |

（A）

（B）

（A）

（B）

1

BLOOD VESSEL TRAINING DEVICE, METHOD, BLOOD VESSEL TRAINING SYSTEM

CROSS-REFERENCE TO RELATED APPLICATION (S)

This application is a national stage application of International Patent Application No. PCT/2022/002827, filed Jan. 26, 2022 (WO 2022/224518 A1, published Oct. 27, 2022), which is herein incorporated by reference in its entirety.

TECHNICAL FIELD

The present embodiments relate to a blood vessel training technology for increasing elasticity of a blood vessel, and more particularly, to a blood vessel training technology that also involves evaluation of improvement of elasticity of a blood vessel.

BACKGROUND ART

There is known blood flow restriction training, which is training for enhancing muscle strength by restricting blood flow. The origin thereof is a training method known in Japan as "Kaatsu training (trademark)." The blood flow restriction training, which has become widespread after JP 2670421 B2 was issued, enlarges muscle based on the following principle.

General training that is performed to enlarge muscle is, for example, to apply a load to the muscle through exercise using a heavy object to cause damage thereto. The damaged muscle notifies the brain of the fact of having been damaged. After this, the brain secretes growth hormone for recovery of the muscle. The growth hormone enters the blood flow and reaches the damaged muscle. The muscle that has received the growth hormone recovers to a state of being slightly larger than the muscle immediately before being damaged. This is so-called "super-recovery." Each time the muscle is damaged through the training, the muscle is gradually enlarged. This is the principle by which the muscle is enlarged through the general training.

Meanwhile, as training for enlarging muscle through a mechanism different therefrom, there is blood flow restriction training. To carry out the blood flow restriction training, a belt (which may be a member such as a pneumatic cuff) is used to tighten an appropriate portion, for example, a vicinity of a proximal end, of a limb of a subject. When a tightening force thereof is appropriate, there is caused a state in which arteries located deep when viewed from the surface of the limb are hardly occluded but veins located shallower than the arteries are occluded to some extent.

Thus, in the limb that has been brought into a state in which blood is supplied through the arteries but it is difficult to deliver blood through the veins, a larger amount of blood is accumulated (pooled) than under a normal state. The accumulated blood flows into capillary vessels of the limb in which blood normally does not flow.

When the blood flow restriction training is not performed, a typical case in which blood flows into the capillary vessels in which blood normally does not flow is a case in which exercise is being performed. That is, when the blood flow restriction training is performed, even in a case in which the subject does not perform any exercise at all during the blood flow restriction training, the same state as that in which exercise is being performed is reproduced in terms of the blood flow in the limb. At this time, the muscle misunderstands, so to speak, that the muscle is being damaged due to intense exercise being performed, and transmits the fact of having been damaged to the brain in the same manner as when the general training is carried out. The subsequent process is the same as when the general training is carried out. The brain notified by the muscle that the muscle has been damaged secretes growth hormone in the same manner as when the general training is carried out. In this manner, each time the blood flow restriction training is performed, the super-recovery is repeated, and the muscle is gradually enlarged.

This is the principle by which the muscle is enlarged through the blood flow restriction training.

The blood flow restriction training is performed to enhance muscle by applying a load caused by blood flow obstruction to the muscle, and therefore has a significant advantage in that no exercise is required in order to enhance the muscle. This means that, for example, muscle enlargement can be caused even in a person with disabilities or an elderly person who has difficulty in performing exercise. In addition, the blood flow restriction training can compensate for an amount of load applied to the muscle by applying a load caused by the blood flow obstruction to the muscle, and therefore has an advantage in that, when the blood flow restriction training is combined with exercise, the load caused by exercise can be reduced to a lower level than before. This advantage produces effects in that, due to the decreased amount of exercise to be performed by the muscle, a fear of damaging joints and muscle can be reduced and a training period can be shortened.

The blood flow restriction training having such advantages as described above has been developed for the purpose of enlarging muscle as has already been described. However, during the development, an effect different from the enlargement of muscle was found.

That effect is an effect of improving elasticity of a blood vessel, which is caused by the blood flow obstruction that is essential for the blood flow restriction training. A mechanism by which such an effect occurs is described below, but before that, a general mechanism for achieving the elasticity of the blood vessel is described first.

Blood flow intermittently enters arteries by a heartbeat. The blood flow proceeds through a blood vessel in accordance with relaxation and contraction of the blood vessel. A flow velocity is lower in a blood vessel that is softer and more flexible, and is higher in a blood vessel that is harder due to arteriosclerosis or the like. Incidentally, that situation can be observed through a pulse wave. The pulse wave is a change in blood pressure or volume caused in a peripheral vascular system in accordance with the heartbeat.

The blood flow delivered in a systolic period of a heart proceeds while expanding an inner wall of the blood vessel. At this time, there is generated such a stress as to rub against a vascular endothelium. This stress is generally called "shear stress." This shear stress becomes larger as the blood vessel has higher elasticity. The flow velocity becomes lower as the blood vessel has higher elasticity because a reaction of the shear stress acts on the blood flow from the inner wall of the blood vessel, to thereby deplete the kinetic energy of the blood flow. As the blood vessel has higher elasticity, a blood vessel diameter is more greatly changed when a certain volume of blood pushed out of the heart passes through the blood vessel, and hence a change in blood pressure or volume in the blood vessel is exhibited to a larger extent. That is, as the blood vessel has higher elasticity, the pulse wave amplitude is exhibited to a larger extent.

Incidentally, it is said that, when the shear stress is applied to the vascular endothelium, vascular endothelial cells are activated to produce NO (nitric oxide). Description of a mechanism by which NO is generated by the shear stress acting on the vascular endothelium is omitted, but it is known that NO acts on and relaxes vascular smooth muscle. Thus, when NO is produced and the elasticity of the blood vessel is increased by the action of NO, the shear stress generated by the blood flow is further increased, and furthermore NO is produced. Therefore, a favorable circulation in which the elasticity of the blood vessel is further increased is achieved.

Now, the description is again focused on the blood flow restriction training.

When the blood flow restriction training is performed, as described above, there is caused a state in which blood flow progresses through the arteries of the limb but it is difficult to deliver blood flow through the veins, and more blood is accumulated in the limb than in a normal time. To end the blood flow restriction training, the belt near the proximal end of the limb is loosened. Then, the blood accumulated in the limb is delivered from the veins at a high rate, and the blood in the arteries, which has been flowing at a decreased rate, also starts to flow at an increased rate. In this manner, a large shear stress is generated on the inner wall of the blood vessel, and a large amount of NO is produced.

Further, it is assumed that, for example, light exercise is performed while the blood flow restriction training is performed. The exercise may be performed through exercise such as curling using a dumbbell, or may be performed through light exercise such as a hand open-and-close exercise in which a hand is repeatedly opened and closed. In any case, when the exercise is performed, the tightening force applied to the limb by the belt changes due to widening and narrowing of the muscle of the limb in a part thereof to which the belt is attached. This causes the blood flowing through the arteries and the veins to repeatedly increase or decrease in velocity. When the blood flow velocity increases, a large amount of NO is produced.

It is already publicly known that, when the blood flow restriction training is performed, more NO is produced than in the normal time in this manner. It is also already publicly known that, when the blood flow restriction training is performed, the blood vessel increases in elasticity due to NO produced more than in the normal time. Normally, NO has a half-life of three seconds to six seconds, and a period during which the elasticity of the blood vessel is increased by NO is not so long. However, under the blood flow restriction training, a concentration of oxygen in the blood is lowered due to the obstruction of the blood flow, and hence the half-life of NO is longer than three seconds to six seconds. Accordingly, under the blood flow restriction training, NO mainly generated in the limb travels along the blood flow to reach portions in the body distant from the limb, and increases the elasticity of the blood vessels, ideally, throughout the body.

As described above, the blood flow restriction training has an effect of increasing the elasticity of the blood vessel. When the elasticity of the blood vessel is lost due to arteriosclerosis or the like, NO production deteriorates, and hence there occurs a vicious cycle in which the blood vessel increasingly loses elasticity. When the blood flow restriction training is regularly performed, it can be expected that the arteriosclerosis may be prevented.

When the elasticity of the blood vessel has increased, it is extremely likely that the blood pressure may decrease. Therefore, the blood flow restriction training is potentially capable of achieving improvement of hypertension, which cannot be treated without depending on drugs at present. Further, the increase in elasticity of the blood vessel improves the blood flow to stagnant capillary vessels, and is therefore also expected to promote health and produce aesthetic effect through supply of nutrients and oxygen.

CITATION LIST

Patent Literature

[PTL 1] JP 5255722 B1

SUMMARY

Technical Problem

Incidentally, when blood flow restriction training is performed for the purpose of increasing elasticity of a blood vessel (in the present application, the blood flow restriction training to be used for such a purpose is referred to as "blood vessel training" or "blood vessel training method"), in order to provide a subject with motivation to continuously perform the blood vessel training method, it is useful for the subject to know how much elasticity has been achieved by the blood vessel of the subject as a result of carrying out the blood vessel training method.

However, at present, there is no technology for allowing the subject to know how much elasticity has been achieved by the blood vessel as a result of carrying out the blood vessel training method.

The present embodiments may provide a technology for allowing a subject to know how much elasticity has been achieved by a blood vessel as a result of carrying out a blood vessel training method.

Solution to Problem

In order to solve the above-mentioned problem, the inventor of the present application proposes the following embodiments.

Embodiments of the present application provide a blood vessel training device, which is configured to form a blood vessel training system for increasing elasticity of a blood vessel in combination with: a tightener including: a belt having a length that allows the belt to be wrapped around a predetermined portion of any one of limbs of a subject; a fixing member configured to fix the belt under a state in which the belt is wrapped around the predetermined portion of the one of the limbs; and a gas bladder, which is provided to the belt, and is configured to apply a predetermined tightening pressure to the predetermined portion of the one of the limbs by tightening the predetermined portion of the one of the limbs through loading of a gas inside the gas bladder under a state in which the belt wrapped around the predetermined portion of the one of the limbs is fixed by the fixing member; a pressure varying device configured to set a pressure of the gas inside the gas bladder to a desired pressure; and a pulse wave measuring device configured to measure, in a vicinity of a portion of the one of the limbs at which the tightener is fixed or on a further distal end side of the one of the limbs relative to the portion, a predetermined parameter varying in accordance with a variation of a magnitude of a pulse wave of an artery, and generate pulse wave data on a pulse wave amplitude based on the predetermined parameter.

The blood vessel training device includes: a control module configured to receive the pulse wave data from the pulse wave measuring device and control the pressure varying device; and a recording unit configured to record data.

The control module of the blood vessel training device is configured to execute: pre-processing for: controlling the pressure varying device so as to cause the pressure varying device to execute a first phase, which is processing including at least changing the pressure of the gas inside the gas bladder so as to pass a range in which the pulse wave amplitude is expected to become maximum; performing at least processing for receiving the pulse wave data a plurality of times from the pulse wave measuring device while the first phase is being executed, to thereby identify a pre-maximum pulse wave amplitude, which is a pulse wave amplitude that became maximum while the first phase was being executed, and a maximum pulse wave pressure, which is the pressure of the gas inside the gas bladder at a time at which the pre-maximum pulse wave amplitude occurred; and recording the pre-maximum pulse wave amplitude and the maximum pulse wave pressure in the recording unit; treatment processing for controlling the pressure varying device so as to cause the pressure varying device to execute a second phase, which is processing for executing a predetermined calculation operation on the maximum pulse wave pressure recorded in the recording unit to obtain a treatment pressure, which is a pressure smaller than the maximum pulse wave pressure, keeping the pressure of the gas inside the gas bladder during a predetermined time period between 1 minute and 15 minutes at such a ratio that a time period in which the pressure of the gas inside the gas bladder is equal to or smaller than the treatment pressure and equal to or larger than 30 mmHg is 50% or larger and a time period in which the pressure of the gas inside the gas bladder is smaller than 30 mmHg is 50% or smaller, and then decreasing the pressure of the gas inside the gas bladder to smaller than 30 mmHg, the treatment processing being executed subsequently to the pre-processing; post-processing for: controlling the pressure varying device so as to cause the pressure varying device to execute a third phase, which is processing for changing the pressure of the gas inside the gas bladder within at least a range of ±10 mmHg of the maximum pulse wave pressure recorded in the recording unit so as to pass the maximum pulse wave pressure, or keeping the pressure of the gas inside the gas bladder within a range equal to or larger than the maximum pulse wave pressure recorded in the recording unit and equal to or smaller than a pressure larger by 20 mmHg than the maximum pulse wave pressure recorded in the recording unit, during a period between a start point, which is a predetermined timing at which 45 seconds have not elapsed from an end of the treatment processing, and an end point, which is a predetermined timing at which at least 100 seconds have elapsed from the end of the treatment processing; performing processing for receiving the pulse wave data a plurality of times from the pulse wave measuring device while the third phase is being executed, to thereby identify a post-maximum pulse wave amplitude, which is a pulse wave amplitude that became maximum while the third phase was being executed; and recording the post-maximum pulse wave amplitude in the recording unit, the post-processing being executed subsequently to the treatment processing; and evaluation processing for evaluating a state of the blood vessel of the subject through use of the pre-maximum pulse wave amplitude and the post-maximum pulse wave amplitude that are recorded in the recording unit, the evaluation processing being executed after the post-processing.

This blood vessel training device is a device for forming the blood vessel training system in combination with the tightener, the pressure varying device, and the pulse wave measuring device.

The tightener to be used in combination with the blood vessel training device according to embodiments of the present application includes: a belt having a length that allows the belt to be wrapped around a predetermined portion of any one of limbs; a fixing member configured to fix the belt under a state in which the belt is wrapped around the predetermined portion of the limb; and a gas bladder, which is provided to the belt, and is configured to apply a predetermined tightening pressure to the predetermined portion of the limb by tightening the predetermined portion of the limb through loading of a gas inside the gas bladder under a state in which the belt wrapped around the predetermined portion of the limb is fixed by the fixing member. For example, the tightener can be formed similarly to a cuff to be generally used for measuring the blood pressure, or can be formed similarly to a pneumatic belt to be used in a blood flow restriction training method. The number of tighteners may be only one, and the limb to which the tightener is attached is generally an arm. A width and a length of the tightener are selected as appropriate depending on the limb to which the tightener is attached.

The pressure varying device to be used in combination with the blood vessel training device according to embodiments of the present application is a device for setting a pressure of the gas inside the gas bladder included in the tightener to a desired pressure. Specifically, the pressure varying device can be formed of a pump, a valve, or the like. The gas to be injected into the gas bladder is generally air, but is not limited thereto.

The pulse wave measuring device to be used in combination with the blood vessel training device according to embodiments of the present application is a device that measures, in a vicinity of a portion of the limb at which the tightener is fixed or on a further distal end side of the limb relative to the portion, a predetermined parameter varying in accordance with a variation of a magnitude of a pulse wave of an artery, and generates pulse wave data on a pulse wave amplitude based on the predetermined parameter. The pulse wave amplitude in the vicinity of the portion at which the tightener is fixed or on the distal end side of the limb from the portion is measured. This is for enabling the pulse wave measuring device to detect the pulse wave of the artery on which a tightening effect is exerted by the tightener. The pulse wave measuring device, as well as the above-mentioned pressure varying device, may have at least some of components of those devices included in the blood vessel training device as parts of the blood vessel training device.

This blood vessel training device is capable of not only carrying out the blood vessel training that produces the blood vessel training effect but also evaluating a degree of change in elasticity of the blood vessel before and after the blood vessel training. That is, the blood vessel training device according to the present application has both an aspect of the blood vessel training device and an aspect of an evaluation device for the elasticity of the blood vessel. The blood vessel training device according to embodiments of the present application, which is a single device that covers those two aspects, is therefore convenient for a subject (or a practitioner who carries out the blood vessel training method on the subject (or uses the blood vessel training method to treat the subject)) who is otherwise required to prepare a plurality of devices depending on those purposes, and is also advantageous in terms of cost.

As described above, the blood vessel training device according to embodiments of the present application is obtained by combining the blood vessel training device and the evaluation device for the elasticity of the blood vessel together, but processing to be executed by the blood vessel training device is not limited to processing for evaluating the elasticity of the blood vessel after the blood vessel training is performed. In addition to such processing, the blood vessel training device may be able to execute only processing required for the blood vessel training when no evaluation is required.

This blood vessel training device includes: a control module having a function of receiving pulse wave data from the pulse wave measuring device and a function of controlling the pressure varying device; and a recording unit for recording data. Further, the control module of the blood vessel training device according to embodiments of the present application sequentially executes four kinds of processing, namely, pre-processing, treatment processing, post-processing, and evaluation processing, which are described later.

Briefly speaking, the pre-processing is processing for measuring the elasticity of the blood vessel before execution of the blood flow restriction training method. The treatment processing is processing for executing the blood flow restriction training method. The post-processing is processing for measuring the elasticity of the blood vessel after the execution of the blood flow restriction training method. Further, the evaluation processing is processing for evaluating how much elasticity has been achieved by the blood vessel of the subject based on the elasticity of the blood vessel before the execution of the blood flow restriction training method, which has been measured in the pre-processing, and the elasticity of the blood vessel after the execution of the blood flow restriction training method, which has been measured in the post-processing.

Now, the above-mentioned four kinds of processing are described in order.

The pre-processing executed by the control module is processing for: controlling the pressure varying device so as to cause the pressure varying device to execute a first phase, which is processing including at least changing the pressure of the gas inside the gas bladder so as to pass a range in which the pulse wave amplitude is expected to become maximum; performing at least processing for receiving the pulse wave data a plurality of times from the pulse wave measuring device while the first phase is being executed, to thereby identify a pre-maximum pulse wave amplitude, which is a maximum pulse wave amplitude that became maximum while the first phase was being executed, and a maximum pulse wave pressure, which is the pressure of the gas inside the gas bladder at a time at which the pre-maximum pulse wave amplitude occurred; and recording the pre-maximum pulse wave amplitude and the maximum pulse wave pressure in the recording unit.

As described above, the pre-processing is for measuring the elasticity of the blood vessel of the subject before execution of the treatment processing, in other words, in a normal state. Therefore, the pre-processing is executed under a state in which the subject is in a resting state.

In the pre-processing, the measurement of the pulse wave amplitude is performed a plurality of times (for example, a large number of times from about several times to about several tens of times per second) while the pressure of the gas inside the gas bladder is being changed so as to pass the range in which the pulse wave amplitude is expected to become maximum. Then, the control module identifies the pre-maximum pulse wave amplitude, which is the pulse wave amplitude that became maximum while the first phase was being executed, and the maximum pulse wave pressure, which is the pressure of the gas inside the gas bladder at the time at which the pre-maximum pulse wave amplitude occurred, and records the pre-maximum pulse wave amplitude and the maximum pulse wave pressure. For example, it is assumed that, in at least a part of a time slot in which the first phase is executed, the pressure of the gas inside the gas bladder decreases linearly so as to pass the range in which the pulse wave amplitude is expected to become maximum. In this case, the pulse wave amplitude gradually increases, becomes maximum at some time point, and then gradually decreases. The pulse wave amplitude draws an upwardly convex parabolic graph. For example, the amplitude of the pulse at its maximum in the graph is identified as the pre-maximum pulse wave amplitude, which is the maximum pulse wave amplitude that occurred in the pre-processing, and the pressure of the gas inside the gas bladder at the time at which the pre-maximum pulse wave amplitude occurred is identified as the maximum pulse wave pressure.

The pulse wave amplitude becomes maximum when an air inside the gas bladder is approximately close to an pressure intermediate point between the systolic blood pressure and the diastolic blood pressure of the subject. A reason why the pulse wave amplitude draws the upwardly convex parabolic graph is as follows.

A force is exerted on the vascular wall, in the first place, from the blood flowing in the blood vessel toward the outer side. This is the blood pressure. The blood pressure is normally constant when the subject is in a resting state.

Under such a state, the limb is compressed from the outer side by the gas bladder. Here, it is assumed that, as an example, the pressure of the gas inside the gas bladder is decreased. In a process of decreasing the pressure of the gas inside the gas bladder, the force applied to the vascular wall from the outer side gradually decreases. First, the pressure of the gas inside the gas bladder is large, and hence the force exerted on the blood vessel from the outer side is larger than the blood pressure. Thus, at this time, an inward force is exerted on the vascular wall. As the pressure of the gas inside the gas bladder decreases, the force applied to the vascular wall from the outer side decreases to be eventually balanced with a force by which the blood pushes the vascular wall outward from the inner side. That is, in the vascular wall, the blood pressure and the pressure of the gas inside the gas bladder are balanced. In this state, no tension is applied to the vascular wall. Further, as the pressure of the gas inside the gas bladder decreases, the force by which the blood pushes the vascular wall outward becomes larger than the force applied to the vascular wall from the outer side, thereby leading to a state in which an outward force is exerted on the vascular wall. As the pressure of the gas inside the gas bladder further decreases, the outward force exerted on the vascular wall gradually increases.

In this manner, the tension exerted on the vascular wall first acts inward, then gradually decreases to become zero, and after that, gradually increases outward. The vascular wall at a time at which no tension is exerted thereon is in a state in which no tension is applied with the outward force and the inward force canceling each other. Assume that the vascular wall is made of an elastic material such as rubber. For example, further stretching of a stretched rubber requires a larger force than stretching an unstretched rubber. As long as the outward force or the inward force is exerted on the vascular wall, when a certain volume of blood flow is about to pass through the blood vessel, the vascular wall cannot expand excessively outward, and an instantaneous decrease in blood pressure caused by expansion of the vascular wall does not occur so much. Meanwhile, in a case in which the tension applied to the vascular wall is zero, when the certain volume of blood flow is about to pass through the vascular, the vascular wall expands greatly outward, and an instantaneous decrease in blood pressure caused by the expansion of the vascular wall increases. Therefore, as the pressure of the gas inside the gas bladder is gradually decreased, the pulse wave amplitude gradually increases, becomes maximum at a certain time point, and then decreases. The upwardly convex graph regarding the pulse wave amplitude is similarly exhibited when the pressure of the gas inside the gas bladder is increasingly applied so as to pass a pressure at which the maximum pulse wave amplitude is expected to occur. In other words, when the pressure of the gas inside the gas bladder is changed so as to pass the pressure at a time at which the maximum pulse wave amplitude occurs, no matter how the pressure of the gas inside the gas bladder is changed, the pressure of the gas inside the gas bladder passes the maximum pulse wave pressure at some time point, and hence the pre-maximum pulse wave amplitude is exhibited at a time point at which the pressure of the gas inside the gas bladder reaches the maximum pulse wave pressure.

As is apparent from the above description, identifying the pre-maximum pulse wave amplitude refers to identifying the maximum pulse wave amplitude that can occur under a state in which no tension is applied to the blood vessel when the subject is in a resting state, that is, which can occur based on original elasticity of the vascular wall of the subject (that is, which ignores a level of blood pressure of the subject). Further, identifying the maximum pulse wave pressure refers to identifying the pressure of the gas inside the gas bladder at a time at which the state in which no tension was applied to the blood vessel of the subject occurred.

The control module records, in the recording unit, the pre-maximum pulse wave amplitude and the maximum pulse wave pressure that have been identified.

It has been described above that the tension generated in the vascular wall becomes zero when the blood pressure and the pressure of the gas inside the gas bladder are balanced. However, this description may lack some accuracy. This is attributable to the fact that the tightener to be used in combination with the blood vessel training device according to embodiments of the present application may apply some extent of tightening force to the predetermined portion of the limb (for example, a tightening force of 30 mmHg or smaller; this tightening force is referred to as "wearing pressure") under a state in which the tightener is attached to the limb (even when the pressure of the gas inside the gas bladder is a normal pressure), and hence in such a case, a pressure obtained by adding the wearing pressure to the air pressure inside the gas bladder corresponds to the tightening force to be actually applied to the limb by the tightener. That is, when such a fact is also taken into consideration, it is more accurate to state that the tension generated in the vascular wall becomes zero when the blood pressure is balanced with "the pressure of the gas inside the gas bladder or the tightening force applied to the limb by the tightener" rather than when the blood pressure is balanced with the pressure of the gas inside the gas bladder.

Next, the treatment processing to be executed by the control module subsequently to the pre-processing is processing for controlling the pressure varying device so as to cause the pressure varying device to execute a second phase, which is processing for executing a predetermined calculation operation on the maximum pulse wave pressure recorded in the recording unit to obtain a treatment pressure, which is a pressure smaller than the maximum pulse wave pressure, keeping the pressure of the gas inside the gas bladder during a predetermined time period between 1 minute and 15 minutes at such a ratio that a time period in which the pressure of the gas inside the gas bladder is equal to or smaller than the treatment pressure and equal to or larger than 30 mmHg is 50% or larger and a time period in which the pressure of the gas inside the gas bladder is smaller than 30 mmHg is 50% or smaller, and then decreasing the pressure of the gas inside the gas bladder to smaller than 30 mmHg.

As described above, the treatment processing is processing for executing the blood flow restriction training on the subject. When the treatment processing is to be executed, the control module causes the pressure varying device to adjust the pressure of the gas inside the gas bladder so that the tightener applies an appropriate tightening force to the limb of the subject. The pressure of the gas is in a range equal to or smaller than the treatment pressure and equal to or larger than 30 mmHg.

The pressure of the gas inside the gas bladder is kept within this range for the following reason.

The treatment processing has an object to increase an amount of NO to be produced by restricting the blood flow proceeding through the blood vessel of the subject to an appropriate range and thereby increase the elasticity of the blood vessel. As described above, the maximum pulse wave pressure, which is the pressure of the gas inside the gas bladder at the time at which the pre-maximum pulse wave amplitude occurred, is the pressure of the gas inside the gas bladder at the time at which no tension is applied to the vascular wall of the subject. Therefore, originally, when the pressure of the gas inside the gas bladder is set to the maximum pulse wave pressure, there occurs a state in which no tension is applied to the vascular wall, that is, a state in which the pre-maximum pulse wave amplitude occurs and the vascular wall is maximally deformed by the force from the blood flow, and hence the amount of NO to be produced becomes maximum. However, under the state in which no tension is applied to the vascular wall, the subject may feel vibration of the blood vessel that is not normally perceived. This phenomenon becomes apparent in a form in which the subject feels a throbbing pulsation, and the subject may feel some fear and sometimes pain. In view of this, in embodiments of the present application, the control module executes the predetermined calculation operation on the maximum pulse wave pressure to obtain the treatment pressure, which is a pressure smaller than the maximum pulse wave pressure, and sets the treatment pressure as an upper limit of the pressure of the gas inside the gas bladder in the second phase, which is executed when the treatment processing is executed. This prevents the subject from feeling any fear or pain described above. The calculation operation performed on the maximum pulse wave pressure in order to obtain the treatment pressure can be performed by, for example, subtracting a certain pressure (e.g., 10 mmHg to 50 mmHg) from the maximum pulse wave pressure or multiplying the maximum pulse wave pressure by a predetermined value (e.g., 0.6 to 0.9) between 0 and 1. Meanwhile, a lower limit of the pressure of the gas inside the gas bladder at the time at which the second phase is executed is set to 30 mmHg in the present application. This value defines the minimum pressure required for performing the blood flow restriction so as to generate sufficient NO in the blood vessel of the limb of the subject. Therefore, when the lower limit of the pressure of the gas inside the gas bladder is set to 30 mmHg, a sufficient amount of NO is produced in the blood vessel of the subject.

When the treatment processing is being executed, the subject may maintain the resting state or may perform light exercise such as the above-mentioned hand open-and-close exercise. It is to be understood that performing light exercise promotes the production of NO for the reason described above.

In the second phase, a time period in which the pressure of the gas inside the gas bladder is kept within the above-mentioned range is a predetermined time length between 1 minute and 15 minutes. A lower limit of the time length is set to 1 minute because 1 minute is sufficient for causing a change in elasticity of the blood vessel before and after the blood flow restriction training method is carried out. In the second phase, an upper limit of the time period in which the pressure of the gas inside the gas bladder is kept within the above-mentioned range is set to 15 minutes in embodiments of the present application. When the pressure is applied to the limb for a longer time period, a burden on a body of the subject may be excessively increased, or the subject may be bored.

In the above-mentioned predetermined time period between 1 minute and 15 minutes in which the second phase is executed, a ratio of the time period in which the pressure of the gas inside the gas bladder is equal to or smaller than the treatment pressure and equal to or larger than 30 mmHg is kept at 50% or larger, and a ratio of the time period in which the pressure of the gas inside the gas bladder is smaller than 30 mmHg is kept at 50% or smaller. This means that the pressure of the gas inside the gas bladder may vary so as to pass through the range equal to or larger than 30 mmHg and the range smaller than 30 mmHg. The wording "may vary" implies that varying is not required. Further, a time slot in which the pressure of the gas inside the gas bladder exceeds 30 mmHg may occupy 100% of the above-mentioned predetermined time period between 1 minute and 15 minutes, that is, the entire time slot. Those points are described later.

In the second phase, after a lapse of the above-mentioned time period, the pressure of the gas inside the gas bladder is decreased to smaller than 30 mmHg. With this, the blood accumulated in the limb flows out of the vein. This causes NO to be supplied from the limb of the subject toward the entire body even when the half-life of NO of three seconds to six seconds is taken into consideration (under hypoxia condition, the half-life of NO may be longer than three seconds to six seconds), and hence the elasticity of, for example, a systemic blood vessel of the subject increases. It is to be understood that, because of being 30 mmHg, the pressure of the gas inside the gas bladder may be decreased to the normal pressure.

The post-processing to be executed by the control module subsequently to the treatment processing is processing for: controlling the pressure varying device so as to cause the pressure varying device to execute a third phase, which is processing for changing the pressure of the gas inside the gas bladder within at least a range of ±10 mmHg of the maximum pulse wave pressure recorded in the recording unit so as to pass the maximum pulse wave pressure, or keeping the pressure of the gas inside the gas bladder within a range equal to or larger than the maximum pulse wave pressure recorded in the recording unit and equal to or smaller than a pressure larger by 20 mmHg than the maximum pulse wave pressure recorded in the recording unit, during a period between a start point, which is a predetermined timing at which 45 seconds have not elapsed from an end of the treatment processing, and an end point, which is a predetermined timing at which at least 100 seconds have elapsed from the end of the treatment processing; performing processing for receiving the pulse wave data a plurality of times from the pulse wave measuring device while the third phase is being executed, to thereby identify a post-maximum pulse wave amplitude, which is a pulse wave amplitude that became maximum while the third phase was being executed; and recording the post-maximum pulse wave amplitude in the recording unit.

As described above, the post-processing is processing for measuring the elasticity of the blood vessel after the execution of the treatment processing. Therefore, the post-processing is executed under a state in which the subject is in a resting state.

In the post-processing, the pressure of the gas inside the gas bladder during the period between the start point, which is the predetermined timing at which 45 seconds have not elapsed from the end of the treatment processing, and the end point, which is the predetermined timing at which at least 100 seconds have elapsed from the end of the treatment processing, is controlled so as to be one of two types described later.

Then, while the third phase is being executed, in the same manner as in the first phase, the control module performs the processing for receiving the pulse wave data a plurality of times (for example, a large number of times from about several times to about several tens of times per second) from the pulse wave measuring device, and identifies the post-maximum pulse wave amplitude, which is the pulse wave amplitude that became maximum while the third phase was being executed. The post-maximum pulse wave amplitude is recorded in the recording unit by the control module in the same manner as in the pre-maximum pulse wave amplitude.

In the third phase, the processing for receiving the pulse wave data is performed in a time slot between the start point, which is the predetermined timing at which 45 seconds have not elapsed from the end of the treatment processing, and the end point, which is the predetermined timing at which at least 100 seconds have elapsed from the end of the treatment processing, because the post-maximum pulse wave amplitude often occurs during a period between a time point at which 45 seconds have elapsed from the end of the treatment processing and a time point at which 100 seconds have elapsed from the end of the treatment processing. Therefore, in the third phase, it is mostly possible to measure the correct post-maximum pulse wave amplitude by setting a time slot in which the pulse wave amplitude is to be measured to such a range as described above. However, depending on the subject, the post-maximum pulse wave amplitude may occur before or after the above-mentioned range between the start point and the end point. Thus, the start point may be set before the time point at which 45 seconds have elapsed from the end of the treatment processing, or the end point may be set after the time point at which 100 seconds have elapsed from the end of the treatment processing. For example, the start point may be set to a predetermined timing at which 40 seconds have not elapsed since 5 seconds elapsed from the end of the treatment processing. Meanwhile, the end point may be set at a predetermined timing at which 200 seconds have not elapsed since 120 seconds elapsed from the end of the treatment processing. When the start point and the end point are set within such a range, the correct post-maximum pulse wave amplitude can be measured with reliability.

In the time slot between the start point and the end point, the pressure of the gas inside the gas bladder is controlled so as to be one of two types described below.

The first one is obtained by processing for changing the pressure of the gas inside the gas bladder within at least the range of ±10 mmHg of the maximum pulse wave pressure so as to pass the maximum pulse wave pressure recorded in the recording unit. The second one is obtained by processing for keeping the pressure of the gas inside the gas bladder within the range equal to or larger than the maximum pulse wave pressure recorded in the recording unit and equal to or smaller than the pressure larger by 20 mmHg than the maximum pulse wave pressure recorded in the recording unit.

As described above, the pre-maximum pulse wave amplitude identified in the pre-processing is the pulse wave amplitude in the state in which no tension is applied to the vascular wall, which is measured when the pressure of the gas inside the gas bladder is the maximum pulse wave pressure. Therefore, it is reasonable that the pulse wave amplitude to be measured in the post-processing, which serves as a target to be compared to the pre-maximum pulse wave amplitude measured in the pre-processing, is originally supposed to be the pulse wave amplitude in the state in which no tension is applied to the vascular wall. In view of the above-mentioned reason, the pressure of the gas inside the gas bladder at a time at which the third phase in the post-processing is executed is supposed to be the maximum pulse wave pressure identified in the pre-processing.

However, in the treatment processing, the blood flow restriction training is executed, and is expected to cause, in the same manner as when exercise is actually performed, an increase in blood pressure by approximately 10 mmHg or about 20 mmHg at maximum. When such an increase in blood pressure is caused, the pressure of the gas inside the gas bladder for creating a state in which no tension is applied to the vascular wall increases by an amount corresponding to the increase in blood pressure. For example, even when the subject performs the above-mentioned hand open-and-close exercise while the treatment processing is being executed, the blood pressure of the subject may increase to some extent, and the increase in blood pressure correspondingly increases the pressure of the gas inside the gas bladder for creating a state in which no tension is applied to the vascular wall.

When the pressure of the gas inside the gas bladder is changed, under the above-mentioned first control, within at least the range of ±10 mmHg of the maximum pulse wave pressure so as to pass the maximum pulse wave pressure recorded in the recording unit, a pressure at which the tension of the vascular wall is zero is included in the changed pressure of the gas inside the gas bladder with a significant probability. This indicates that a probability of being able to catch the pulse wave amplitude (that is, post-maximum pulse wave amplitude) that becomes maximum when the tension of the vascular wall is zero is significantly high. Therefore, such a change in pressure of the gas inside the gas bladder is effective for identifying the post-maximum pulse wave amplitude, which serves as the target to be compared to the pre-maximum pulse wave amplitude. When the post-maximum pulse wave amplitude is to be detected with higher reliability, the pressure of the gas inside the gas bladder may be changed within at least a range of ±20 mmHg of the maximum pulse wave pressure so as to pass the maximum pulse wave pressure recorded in the recording unit.

Further, when the pressure of the gas inside the gas bladder is kept, under the above-mentioned second control, within the range equal to or larger than the maximum pulse wave pressure recorded in the recording unit and equal to or smaller than the pressure larger by 20 mmHg than the maximum pulse wave pressure recorded in the recording unit, the pressure of the gas inside the gas bladder at that time may not be a pressure at which the tension applied to the vascular wall is zero, but differs by only 20 mmHg at maximum from the pressure at which the tension applied to the vascular wall is zero. Thus, even when the tension applied to the vascular wall is not zero, a state in which the tension applied to the vascular wall is small is kept during a period from the start point to the end point. When the tension applied to the vascular wall is small, the pulse wave amplitude is exhibited to a large extent, and hence such a change in pressure of the gas inside the gas bladder is effective for identifying the post-maximum pulse wave amplitude, which serves as the target to be compared to the pre-maximum pulse wave amplitude. When the second control is performed, the pressure of the gas inside the gas bladder may be kept constant between the upper limit and the lower limit that are described above, or may be changed between the upper limit and the lower limit.

Then, the control module of the blood vessel training device according to embodiments of the present application finally executes the evaluation processing. The evaluation processing is processing for evaluating how much elasticity has been achieved by the blood vessel of the subject based on the elasticity of the blood vessel before the execution of the blood flow restriction training method, which has been measured in the pre-processing, and the elasticity of the blood vessel after the execution of the blood flow restriction training method, which has been measured in the post-processing.

The evaluation processing may be executed immediately after an end of the post-processing, or may be executed at a timing after the end of the post-processing but not immediately after that, for example, when input prompting execution of the evaluation processing is performed on the blood vessel training device.

In the evaluation processing, for example, when the pre-maximum pulse wave amplitude recorded in the recording unit in the pre-processing is represented by $P_B$ and the post-maximum pulse wave amplitude recorded in the recording unit in the post-processing is represented by $P_A$, a result obtained by calculating $P_A/P_B$ Or $(P_A-P_B)/P_B$ can be used as an evaluation result. As described above, the pre-maximum pulse wave amplitude and the post-maximum pulse wave amplitude are measured in states similar to each other, and hence it is meaningful to compare those values as represented by the above-mentioned operational expression.

As described above, the pulse wave measuring device measures, in a vicinity of a portion of the limb at which the tightener is fixed or on a further distal end side of the limb relative to the portion, a predetermined parameter varying in accordance with a variation of a magnitude of a pulse wave of an artery, and generates pulse wave data on a pulse wave amplitude based on the predetermined parameter. The pulse wave measuring device may be able to measure the pressure of the gas inside the gas bladder as the predetermined parameter. This means that so-called cuff pulse wave measurement is employed in embodiments of the present application. In this case, a place at which the pulse wave is measured is a tightener-attached part of the limb to which the tightener is attached.

Meanwhile, a device for measuring a pulse wave at a fingertip, a wrist, or another spot is publicly known or well known, and is even commercially available. Such a device can be used to measure the pulse wave, and when such a pulse wave measuring method is employed in embodiments of the present application, the spot at which the pulse wave is measured is not limited to the tightener-attached part of the limb to which the tightener is attached.

The control module may be configured to execute the pre-processing in a manner described below.

The control module may be configured to, in the pre-processing: control the pressure varying device so as to cause the pressure varying device to execute the first phase, which is processing including causing the pressure varying device to execute processing for decreasing the pressure of the gas inside the gas bladder so as to pass the range in which the pulse wave amplitude is expected to become maximum; perform processing for receiving the pulse wave data a plurality of times from the pulse wave measuring device while the pressure varying device is decreasing the pressure of the gas inside the gas bladder, to thereby identify the pre-maximum pulse wave amplitude, which is the pulse wave amplitude that became maximum while the pressure varying device was decreasing the pressure of the gas inside the gas bladder, and the maximum pulse wave pressure, which is the pressure of the gas inside the gas bladder at the time at which the pre-maximum pulse wave amplitude occurred; and record the pre-maximum pulse wave amplitude and the maximum pulse wave pressure in the recording unit.

As has been described above, the first phase in the pre-processing changes the pressure of the gas inside the gas bladder in a range in which the pre-maximum pulse wave amplitude occurs at some pressure, but this change may be performed so as to decrease the pressure from a pressure above a range in which the pre-maximum pulse wave amplitude is assumed to occur down to a pressure below the range. Pressure reduction of the gas inside the gas bladder can be smoothly achieved only by opening the valve, but it is difficult to smoothly apply the pressure to the gas by the pump. Therefore, when such gas pressure reduction (for example, linear decrease in pressure) is employed in the first phase, the pre-maximum pulse wave amplitude and the maximum pulse wave pressure can be accurately grasped. In this case, the maximum pulse wave amplitude exhibited while the pressure of the gas inside the gas bladder was decreased by the pressure varying device is identified as the pre-maximum pulse wave amplitude, and the pressure of the gas inside the gas bladder at that time is identified as the maximum pulse wave pressure.

Alternatively, the control module may be configured to, in the pre-processing: control the pressure varying device so as to cause the pressure varying device to execute the first phase, which is processing including causing the pressure varying device to execute processing for decreasing the pressure of the gas inside the gas bladder so as to pass the range in which the pulse wave amplitude is expected to become maximum and then maintaining the pressure of the gas inside the gas bladder at a predetermined constant pressure during a period of 5 seconds to 15 seconds; perform processing for receiving the pulse wave data a plurality of times from the pulse wave measuring device while the pressure varying device is decreasing the pressure of the gas inside the gas bladder, to thereby identify a tentative pre-maximum pulse wave amplitude, which is a pulse wave amplitude that became maximum while the pressure varying device was decreasing the pressure of the gas inside the gas bladder, and the maximum pulse wave pressure, which is the pressure of the gas inside the gas bladder at a time at which the tentative pre-maximum pulse wave amplitude occurred; control the pressure varying device so that the predetermined constant pressure of the gas inside the gas bladder maintained during the period of 5 seconds to 15 seconds is the maximum pulse wave pressure; perform processing for receiving the pulse wave data a plurality of times from the pulse wave measuring device while the predetermined constant pressure of the gas inside the gas bladder is kept at the maximum pulse wave pressure, to thereby identify, as the pre-maximum pulse wave amplitude, the pulse wave amplitude that became maximum while the predetermined constant pressure of the gas inside the gas bladder was kept at the maximum pulse wave pressure; and record the identified pre-maximum pulse wave amplitude and the maximum pulse wave pressure in the recording unit.

In the example described immediately before, in the first phase, the pressure of the gas inside the gas bladder is changed so as to decrease the pressure from the pressure above the range in which the pre-maximum pulse wave amplitude is assumed to occur down to the pressure below the range, then the maximum pulse wave amplitude exhibited in that process is identified as the pre-maximum pulse wave amplitude, and the pressure of the gas inside the gas bladder at that time is also identified as the maximum pulse wave pressure. However, in this example, in the same manner as in the example described immediately before, in the first phase, the pressure of the gas inside the gas bladder is changed so as to decrease the pressure from the pressure above the range in which the pre-maximum pulse wave amplitude is assumed to occur down to the pressure below the range, and then the pressure of the gas inside the gas bladder at the time at which the maximum pulse wave amplitude exhibited in that process occurred is identified as the maximum pulse wave pressure, but the pulse wave amplitude at that time is set as a tentative pre-maximum pulse wave amplitude instead of being set as the pre-maximum pulse wave amplitude. The tentative pre-maximum pulse wave amplitude may be recorded in the recording unit, but is not always required to be recorded in the recording unit.

In this example, in the first phase, after the maximum pulse wave pressure is identified, the pressure of the gas inside the gas bladder that has been temporarily lowered is increased until the pressure of the gas inside the gas bladder reaches the maximum pulse wave pressure, and the pulse wave amplitude is measured while being kept constant under that state during a period of 5 seconds to 15 seconds. Then, the maximum pulse wave amplitude exhibited within a period in which the pressure of the gas inside the gas bladder is kept at the maximum pulse wave pressure is adopted anew as the pre-maximum pulse wave amplitude. This processing is performed because a peak of the pulse wave occurs only at a timing of the heartbeat, that is, only once per approximately one second in most cases, and hence a timing at which the maximum pulse wave amplitude occurs while the pressure of the gas inside the gas bladder is changed so as to decrease the pressure from the pressure above the range in which the pre-maximum pulse wave amplitude is assumed to occur down to the pressure below the range sometimes does not match a timing at which the pulse wave measuring device samples a parameter regarding the pulse wave, thereby leading to a fear in that accuracy may be lacking. For example, assuming that the pulse wave measuring device intermittently measures the pulse wave amplitude at timings of several times to several tens of times per second, when the timing at which the maximum pulse wave amplitude occurs falls between timings at which the pulse wave measuring device samples a parameter regarding the pulse wave, it may be inappropriate to set the maximum pulse wave amplitude sampled at a timing before or after that as the pre-maximum pulse wave amplitude.

Meanwhile, when the largest pulse wave amplitude among the pulse wave amplitudes that occurred under a state in which the pressure of the gas inside the gas bladder has been kept at the maximum pulse wave pressure is set as the pre-maximum pulse wave amplitude, the largest pulse wave amplitude among the pulse wave amplitudes that have been sampled a plurality of times under the state in which no tension is applied to the vascular wall is extremely likely to be correctly the maximum pulse wave amplitude for the subject in a normal state, and is therefore suitable as the pre-maximum pulse wave amplitude. In this example, the pre-maximum pulse wave amplitude and the maximum pulse wave pressure that have been determined in such a manner are recorded in the recording unit.

As described above, in the second phase at a time at which the treatment processing is executed, the processing for keeping the pressure of the gas inside the gas bladder during the predetermined time period between 1 minute and 15 minutes at such a ratio that the time period in which the pressure of the gas inside the gas bladder is equal to or smaller than the treatment pressure and equal to or larger than 30 mmHg is 50% or larger and the time period in which the pressure of the gas inside the gas bladder is smaller than 30 mmHg is 50% or smaller, and then decreasing the pressure of the gas inside the gas bladder to smaller than 30 mmHg is executed.

Here, the control module may be configured to, in the treatment processing, control the pressure varying device so as to cause the pressure varying device to execute the second phase, which is processing for keeping the pressure of the gas inside the gas bladder constant throughout the predetermined time period between 1 minute and 15 minutes. In this case, during a time slot selected from the above-mentioned period between 1 minute and 15 minutes in which the second phase is executed, the pressure of the gas inside the gas bladder is continuously kept at a pressure of 30 mmHg or larger and equal to or smaller than the treatment pressure. Therefore, in this case, 100% of the time slot selected from the above-mentioned period between 1 minute and 15 minutes in which the second phase is executed is a time slot in which the pressure of the gas inside the gas bladder is kept at the pressure of 30 mmHg or larger and equal to or smaller than the treatment pressure. When the pressure of the gas inside the gas bladder is continuously kept at 30 mmHg or larger, the tension applied to the vascular wall becomes somewhat smaller than that in the normal time, and hence the shear stress caused between the blood flow and the vascular wall due to the blood flow tends to increase. Thus, production of NO occurring when the treatment processing is executed is promoted.

Further, the control module may be configured to, in the treatment processing, control the pressure varying device so as to cause the pressure varying device to execute the second phase, which is processing for alternately repeating a first time slot in which the pressure of the gas inside the gas bladder is equal to or smaller than the treatment pressure and equal to or larger than 30 mmHg and a second time slot in which the pressure of the gas inside the gas bladder is smaller than 30 mmHg, during the predetermined time period between 1 minute and 15 minutes, so that the first time slot per time ranges over a period between 15 seconds to 35 seconds and the second time slot per time ranges over a period between 15 seconds to 35 seconds.

When the second phase is executed, a first time slot in which the pressure of the gas inside the gas bladder is 30 mmHg or larger and a second time slot in which the pressure of the gas inside the gas bladder is smaller than 30 mmHg are alternately repeated, thereby causing, in the limb of the user, a repetition of the obstruction of the blood flow and promotion of the obstructed blood flow, which is quite similar to that caused when arm curls or leg curls are successively performed. This causes a large shear stress between the inner wall of the blood vessel and the blood flow, and hence the production of NO occurring when the treatment processing is executed is promoted. The first time slot per time is set to 15 seconds or longer because, unless the blood flow is restricted for such a time period, an effect of the blood vessel training is less likely to occur. Further, the first time slot per time period is set to 35 seconds or shorter because, even when the blood flow is restricted for a longer time period, a physical burden on the subject tends to be larger than improvement of the effect. A length of the second slot period per time is set to a length between 15 seconds to 35 seconds because an interval between the obstruction and obstruction of the blood flow is often preferred to be set approximately the same as a time period for the obstruction of the blood flow in consideration of a trade-off between the effect of the blood vessel training and the burden on the body of the subject.

As described above, the pre-maximum pulse wave amplitude identified in the pre-processing is the pulse wave amplitude measured when the pressure of the gas inside the gas bladder is the maximum pulse wave pressure, and it is the pulse wave amplitude in the state in which no tension is applied to the vascular wall.

Therefore, it is reasonable that the post-maximum pulse wave amplitude being the pulse wave amplitude measured in the post-processing, which serves as the target to be compared to the pre-maximum pulse wave amplitude measured in the pre-processing, is supposed to be the pulse wave amplitude in the state in which no tension is applied to the vascular wall. It is at least supposed that, when the post-maximum pulse wave amplitude is measured, the tension applied to the vascular wall is required to be somewhat smaller than that in the normal time.

In view of the above, the control module in embodiments of the present application executes the post-processing as any one of the two kinds of processing that have already been described. The first processing is processing for changing the pressure of the gas inside the gas bladder within at least the range of +10 mmHg of the maximum pulse wave pressure so as to pass the maximum pulse wave pressure recorded in the recording unit. The second processing is processing for keeping the pressure of the gas inside the gas bladder within the range equal to or larger than the maximum pulse wave pressure recorded in the recording unit and equal to or smaller than the pressure larger by 20 mmHg than the maximum pulse wave pressure recorded in the recording unit. When the first processing is executed, the control module may be configured as follows.

The control module may be configured to, in the post-processing: control the pressure varying device so as to cause the pressure varying device to execute the third phase, which is processing for linearly decreasing, during the period between the start point and the end point, the pressure of the gas inside the gas bladder from a range larger than the maximum pulse wave pressure recorded in the recording unit by 10 mmHg or larger and equal to or smaller than a pressure larger by 20 mmHg to a range of a pressure smaller than the maximum pulse wave pressure by at least 10 mmHg; perform processing for receiving the pulse wave data a plurality of times from the pulse wave measuring device while the third phase is being executed, to thereby identify the post-maximum pulse wave amplitude, which is the pulse wave amplitude that became maximum while the third phase was being executed; and record the post-maximum pulse wave amplitude in the recording unit.

In this case, the pressure of the gas inside the gas bladder at the start point is a predetermined pressure that is larger than the maximum pulse wave pressure by 10 mmHg or larger and equal to or smaller than a pressure larger than the maximum pulse wave pressure by 20 mmHg. As described above, the pressure of the gas inside the gas bladder at a time at which the post-maximum pulse wave amplitude occurs is often larger by about 10 mmHg or about 20 mmHg at maximum than the maximum pulse wave pressure as the blood pressure of the subject increases through the treatment processing. Therefore, when the pressure of the gas inside the gas bladder at the start point is set as described above and the pressure of the gas inside the gas bladder is decreased from that point to a predetermined pressure that is smaller than the maximum pulse wave pressure by 10 mmHg or larger, the post-maximum pulse wave amplitude can be grasped with a significant probability.

While time elapses from the start point to the end point, the pressure of the gas inside the gas bladder is linearly decreased between the above-mentioned two pressures. In this case, while the pressure of the gas inside the gas bladder is linearly decreased, the force applied to the vascular wall is first directed inward, becomes zero after a while, and is directed outward after that. Again, when the force applied to the vascular wall is zero, no tension is applied to the vascular wall. In the third phase during the post-processing, when the pressure of the gas inside the gas bladder is linearly decreased as described above, the tension applied to the vascular wall is zero for a moment (or short time period), but in time slots before and after that moment, the tension applied to the vascular wall is small to some extent. The largest pulse wave amplitude among the pulse wave amplitudes measured when such a third phase is being executed is suitable to be identified as the post-maximum pulse wave amplitude, which serves as the target to be compared to the pre-maximum pulse wave amplitude.

When the second processing is executed, the control module may be configured as follows.

The control module may be configured to, in the post-processing: control the pressure varying device so as to cause the pressure varying device to execute the third phase, which is processing for keeping the pressure of the gas inside the gas bladder constant within a range equal to or larger than the maximum pulse wave pressure recorded in the recording unit and equal to or smaller than the pressure larger by 20 mmHg than the maximum pulse wave pressure during the period between the start point and the end point; perform processing for receiving the pulse wave data a plurality of times from the pulse wave measuring device while the third phase is being executed, to thereby identify the post-maximum pulse wave amplitude, which is the pulse wave amplitude that became maximum while the third phase was being executed; and record the post-maximum pulse wave amplitude in the recording unit.

When the pressure of the gas inside the gas bladder is kept constant within the above-mentioned range, the tension applied to the vascular wall can be kept at or close to zero throughout a period in which the pulse wave amplitude is measured in order to measure the post-maximum pulse wave amplitude in the post-processing.

The inventor of the present application further proposes the following blood vessel training system as one mode of embodiments of the present application. An effect of this blood vessel training system is the same as the effect of the blood vessel training device according to embodiments of the present application.

An example of the blood vessel training system is a blood vessel training system including: a tightener including: a belt having a length that allows the belt to be wrapped around a predetermined portion of any one of limbs of a subject; a fixing member configured to fix the belt under a state in which the belt is wrapped around the predetermined portion of the one of the limbs; and a gas bladder, which is provided to the belt, and is configured to apply a predetermined tightening pressure to the predetermined portion of the one of the limbs by tightening the predetermined portion of the one of the limbs through loading of a gas inside the gas bladder under a state in which the belt wrapped around the predetermined portion of the one of the limbs is fixed by the fixing member; a pressure varying device configured to set a pressure of the gas inside the gas bladder to a desired pressure; and a pulse wave measuring device configured to measure, in a vicinity of a portion of the one of the limbs at which the tightener is fixed or on a further distal end side of the one of the limbs relative to the portion, a predetermined parameter varying in accordance with a variation of a magnitude of a pulse wave of an artery, and generate pulse wave data on a pulse wave amplitude based on the predetermined parameter.

The blood vessel training system further includes: a control module configured to receive the pulse wave data from the pulse wave measuring device and control the pressure varying device; and a recording unit configured to record data.

The control module e is configured to execute: pre-processing for: controlling the pressure varying device so as to cause the pressure varying device to execute a first phase, which is processing including at least changing the pressure of the gas inside the gas bladder so as to pass a range in which the pulse wave amplitude is expected to become maximum; performing at least processing for receiving the pulse wave data a plurality of times from the pulse wave measuring device while the first phase is being executed, to thereby identify a pre-maximum pulse wave amplitude, which is a pulse wave amplitude that became maximum while the first phase was being executed, and a maximum pulse wave pressure, which is the pressure of the gas inside the gas bladder at a time at which the pre-maximum pulse wave amplitude occurred; and recording the pre-maximum pulse wave amplitude and the maximum pulse wave pressure in the recording unit; treatment processing for controlling the pressure varying device so as to cause the pressure varying device to execute a second phase, which is processing for executing a predetermined calculation operation on the maximum pulse wave pressure recorded in the recording unit to obtain a treatment pressure, which is a pressure smaller than the maximum pulse wave pressure, keeping the pressure of the gas inside the gas bladder during a predetermined time period between 1 minute and 15 minutes at such a ratio that a time period in which the pressure of the gas inside the gas bladder is equal to or smaller than the treatment pressure and equal to or larger than 30 mmHg is 50% or larger and a time period in which the pressure of the gas inside the gas bladder is smaller than 30 mmHg is 50% or smaller, and then decreasing the pressure of the gas inside the gas bladder to smaller than 30 mmHg, the treatment processing being executed subsequently to the pre-processing; post-processing for: controlling the pressure varying device so as to cause the pressure varying device to execute a third phase, which is processing for changing the pressure of the gas inside the gas bladder within at least a range of +10 mmHg of the maximum pulse wave pressure recorded in the recording unit so as to pass the maximum pulse wave pressure, or keeping the pressure of the gas inside the gas bladder within a range equal to or larger than the maximum pulse wave pressure recorded in the recording unit and equal to or smaller than a pressure larger by 20 mmHg than the maximum pulse wave pressure recorded in the recording unit, during a period between a start point, which is a predetermined timing at which 45 seconds have not elapsed from an end of the treatment processing, and an end point, which is a predetermined timing at which at least 100 seconds have elapsed from the end of the treatment processing; performing processing for receiving the pulse wave data a plurality of times from the pulse wave measuring device while the third phase is being executed, to thereby identify a post-maximum pulse wave amplitude, which is a pulse wave amplitude that became maximum while the third phase was being executed; and recording the post-maximum pulse wave amplitude in the recording unit, the post-processing being executed subsequently to the treatment processing; and evaluation processing for evaluating a state of the blood vessel of the subject through use of the pre-maximum pulse wave amplitude and the post-maximum pulse wave amplitude that are recorded in the recording unit, the evaluation processing being executed after the post-processing.

The inventor of the present application further proposes the following blood vessel training method as one mode of embodiments of the present application. An effect of this blood vessel training method is the same as the effect of the blood vessel training device according to embodiments of the present application.

An example of the blood vessel training method is a blood vessel training method to be executed by a control module of a blood vessel training device, the blood vessel training device being configured to form a blood vessel training system for increasing elasticity of a blood vessel in combination with: a tightener including: a belt having a length that allows the belt to be wrapped around a predetermined portion of any one of limbs of a subject; a fixing member configured to fix the belt under a state in which the belt is wrapped around the predetermined portion of the one of the limbs; and a gas bladder, which is provided to the belt, and is configured to apply a predetermined tightening pressure to the predetermined portion of the one of the limbs by tightening the predetermined portion of the one of the limbs through loading of a gas inside the gas bladder under a state in which the belt wrapped around the predetermined portion of the one of the limbs is fixed by the fixing member; a pressure varying device configured to set a pressure of the gas inside the gas bladder to a desired pressure; and a pulse wave measuring device configured to measure, in a vicinity of a portion of the one of the limbs at which the tightener is fixed or on a further distal end side of the one of the limbs relative to the portion, a predetermined parameter varying in accordance with a variation of a magnitude of a pulse wave of an artery, and generate pulse wave data on a pulse wave amplitude based on the predetermined parameter, the blood vessel training device including: the control module configured to receive the pulse wave data from the pulse wave measuring device and control the pressure varying device; and a recording unit configured to record data.

The blood vessel training method includes executing, by the control module: pre-processing for: controlling the pressure varying device so as to cause the pressure varying device to execute a first phase, which is processing including at least changing the pressure of the gas inside the gas bladder so as to pass a range in which the pulse wave amplitude is expected to become maximum; performing at least processing for receiving the pulse wave data a plurality of times from the pulse wave measuring device while the first phase is being executed, to thereby identify a pre-maximum pulse wave amplitude, which is a pulse wave amplitude that became maximum while the first phase was being executed, and a maximum pulse wave pressure, which is the pressure of the gas inside the gas bladder at a time at which the pre-maximum pulse wave amplitude occurred; and recording the pre-maximum pulse wave amplitude and the maximum pulse wave pressure in the recording unit; treatment processing for controlling the pressure varying device so as to cause the pressure varying device to execute a second phase, which is processing for executing a predetermined calculation operation on the maximum pulse wave pressure recorded in the recording unit to obtain a treatment pressure, which is a pressure smaller than the maximum pulse wave pressure, keeping the pressure of the gas inside the gas bladder during a predetermined time period between 1 minute and 15 minutes at such a ratio that a time period in which the pressure of the gas inside the gas bladder is equal to or smaller than the treatment pressure and equal to or larger than 30 mmHg is 50% or larger and a time period in which the pressure of the gas inside the gas bladder is smaller than 30 mmHg is 50% or smaller, and then decreasing the pressure of the gas inside the gas bladder to smaller than 30 mmHg, the treatment processing being executed subsequently to the pre-processing; post-processing for: controlling the pressure varying device so as to cause the pressure varying device to execute a third phase, which is processing for changing the pressure of the gas inside the gas bladder within at least a range of ±10 mmHg of the maximum pulse wave pressure recorded in the recording unit so as to pass the maximum pulse wave pressure, or keeping the pressure of the gas inside the gas bladder within a range equal to or larger than the maximum pulse wave pressure recorded in the recording unit and equal to or smaller than a pressure larger by 20 mmHg than the maximum pulse wave pressure recorded in the recording unit, during a period between a start point, which is a predetermined timing at which 45 seconds have not elapsed from an end of the treatment processing, and an end point, which is a predetermined timing at which at least 100 seconds have elapsed from the end of the treatment processing; performing processing for receiving the pulse wave data a plurality of times from the pulse wave measuring device while the third phase is being executed, to thereby identify a post-maximum pulse wave amplitude, which is a pulse wave amplitude that became maximum while the third phase was being executed; and recording the post-maximum pulse wave amplitude in the recording unit, the post-processing being executed subsequently to the treatment processing; and evaluation processing for evaluating a state of the blood vessel of the subject through use of the pre-maximum pulse wave amplitude and the post-maximum pulse wave amplitude that are recorded in the recording unit, the evaluation processing being executed after the post-processing.

BRIEF DESCRIPTION OF DRAWINGS

FIG. 4 is a diagram a configuration of a control circuit of the blood vessel training device included in the blood vessel training system illustrated in FIG. 1;

DESCRIPTION OF EMBODIMENTS

Now, one embodiment of the present embodiments is described with reference to the drawings.

Figure 1:
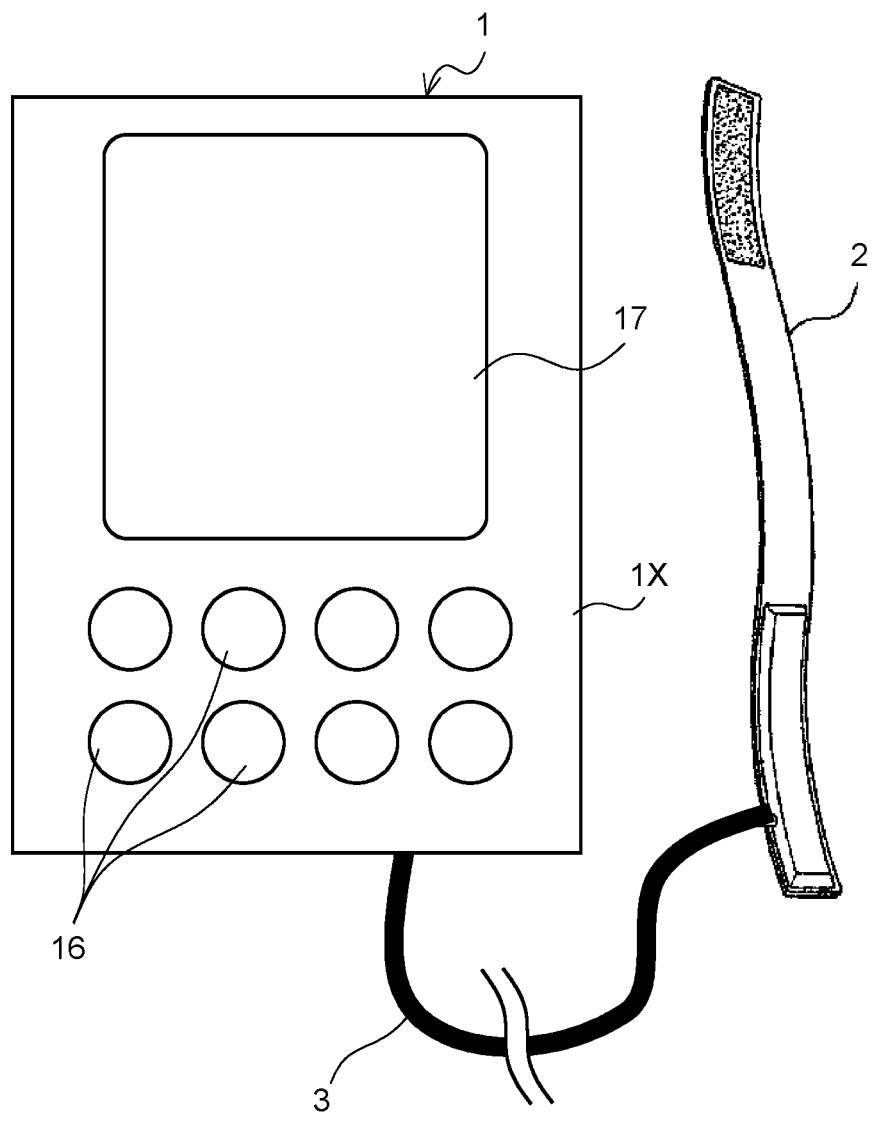
FIG. 1 is a view for illustrating an overall configuration of a blood vessel training system according to a first embodiment of the present embodiments.

FIG. 1 is an illustration of an entire blood vessel training system according to the one embodiment of the present embodiments.

Figure 2:
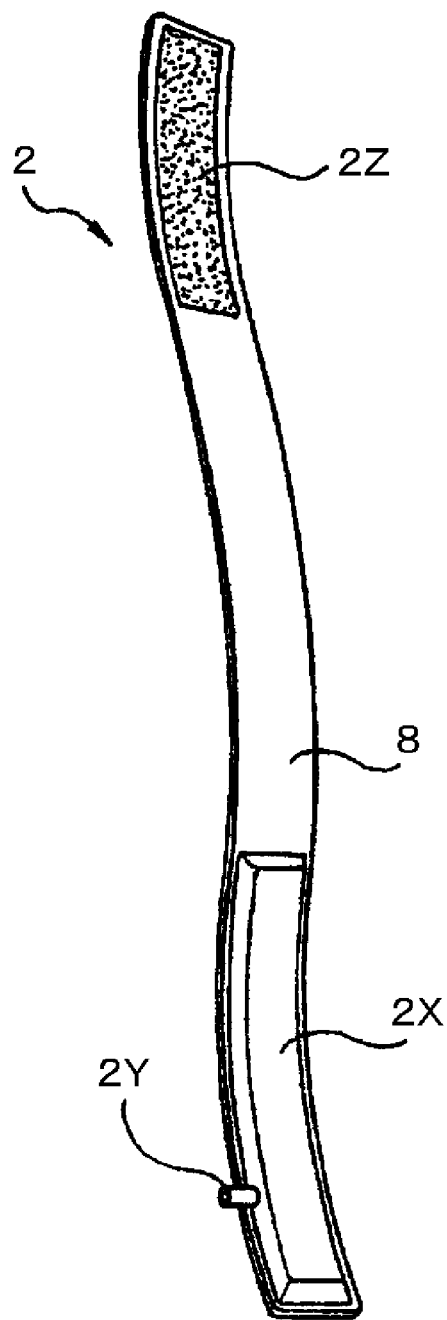
FIG. 2 is a perspective view for illustrating a pressure applying belt included in the blood vessel training system illustrated in FIG. 1.

The blood vessel training system includes a blood vessel training device 1 and a pressure applying belt 2, which is illustrated in detail in FIG. 2. The pressure applying belt 2 corresponds to a tightener referred to in the present application.

First, a configuration of the pressure applying belt 2 is described.

The pressure applying belt 2 is controlled by the blood vessel training device 1 to apply such a tightening force that causes restriction of blood, examples of which include occlusion, to a limb of a subject to which the pressure applying belt 2 is attached. In this embodiment, it is assumed that the limb to which the pressure applying belt 2 is attached is an arm of the subject, but the limb may be a leg.

It suffices that the number of pressure applying belts 2 is one. There are two pressure applying belts 2 when the pressure applying belts 2 are fixed to both arms. In this manner, a required number of pressure applying belts 2 may be prepared. In this embodiment, it is assumed that one pressure applying belt 2 is included in the blood vessel training system, but the present embodiments are not limited thereto.

The pressure applying belt 2 can be configured similarly to a cuff included in a sphygmomanometer, or can be configured similarly to a pneumatic belt supplied along with KAATSU Master (trademark), which is a device for Kaatsu training (trademark) manufactured and sold by KAATSU JAPAN Co., Ltd.

The configuration of the pressure applying belt 2 serving as an example is described.

The pressure applying belt 2 includes an elongated tightening band 8 formed into a belt shape. The tightening band 8 is preferred to be made of a material that does not practically stretch in a length direction of the tightening band 8, for example, a woven fabric that is woven with appropriate threads. The pressure applying belt 2 has a length set to such an extent that there is still some margin after the pressure applying belt 2 is wrapped once around a predetermined portion of the arm to which the pressure applying belt 2 is expected to be attached, for example, a predetermined portion in the vicinity of a base of the arm.

The tightening band 8 has a width set to such an appropriate width that the tightening band 8 is thin enough to prevent the tightening band 8 from overlapping a muscle belly when being attached to the predetermined portion in the vicinity of the base of the arm and is thick enough to prevent the tightening band 8 from biting into the arm to cause pain to the subject. However, the width of the tightening band 8 may be larger, and it is not always required to prevent the tightening band 8 from overlapping the muscle belly when the tightening band 8 is attached to the arm.

For example, on an inner surface of the tightening band 8, an airtight gas bladder 2X, which is made of a material that can withstand an air pressure of about 400 mmHg, is mounted. The gas bladder 2X may be made of a stretchable material such as natural rubber, or may be made of a resin or another material that is substantially non-stretchable. The gas bladder 2X is connected in a communicating state to a coupling tube 2Y, examples of which include a resin tube, and is connected through the coupling tube 2Y to a distal end of a rubber tube 3, which is made of, for example, rubber, and is a tube of which a proximal end is to be connected to the blood vessel training device 1. The gas bladder 2X corresponds to a gas bladder in embodiments of the present application. The gas bladder 2X in this embodiment is provided on the inner surface of the tightening band 8, but the gas bladder 2X may be arranged inside a bag-shaped tightening band 8.

On an inner side of the tightening band 8, there is also provided a fixing portion 2Z that fixes a diameter of a loop formed by the tightening band 8 when the tightening band 8 of the pressure applying belt 2 is wrapped at a predetermined position of the arm of the subject. As long as this fixing is allowed, the fixing portion 2Z may have any configuration. The fixing portion 2Z in this embodiment is a hook-and-loop fastener, but the present embodiments are not limited thereto. When the tightening band 8 is wrapped around the arm of the subject from the lower side of FIG. 2 to fix the fixing portion 2Z to an outer surface of the tightening band 8, the diameter of the loop formed by the tightening band 8 is fixed.

Under a state in which the pressure applying belt 2 is fixed to an appropriate part of the arm of the subject, air is supplied into or discharged from the gas bladder 2X of the pressure applying belt 2 through the rubber tube 3 by the blood vessel training device 1. The pressure of the air causes the pressure applying belt 2 to apply a tightening force at an appropriate pressure to the arm of the subject to which the pressure applying belt 2 is attached.

Next, the blood vessel training device 1 is described.

Figure 3:
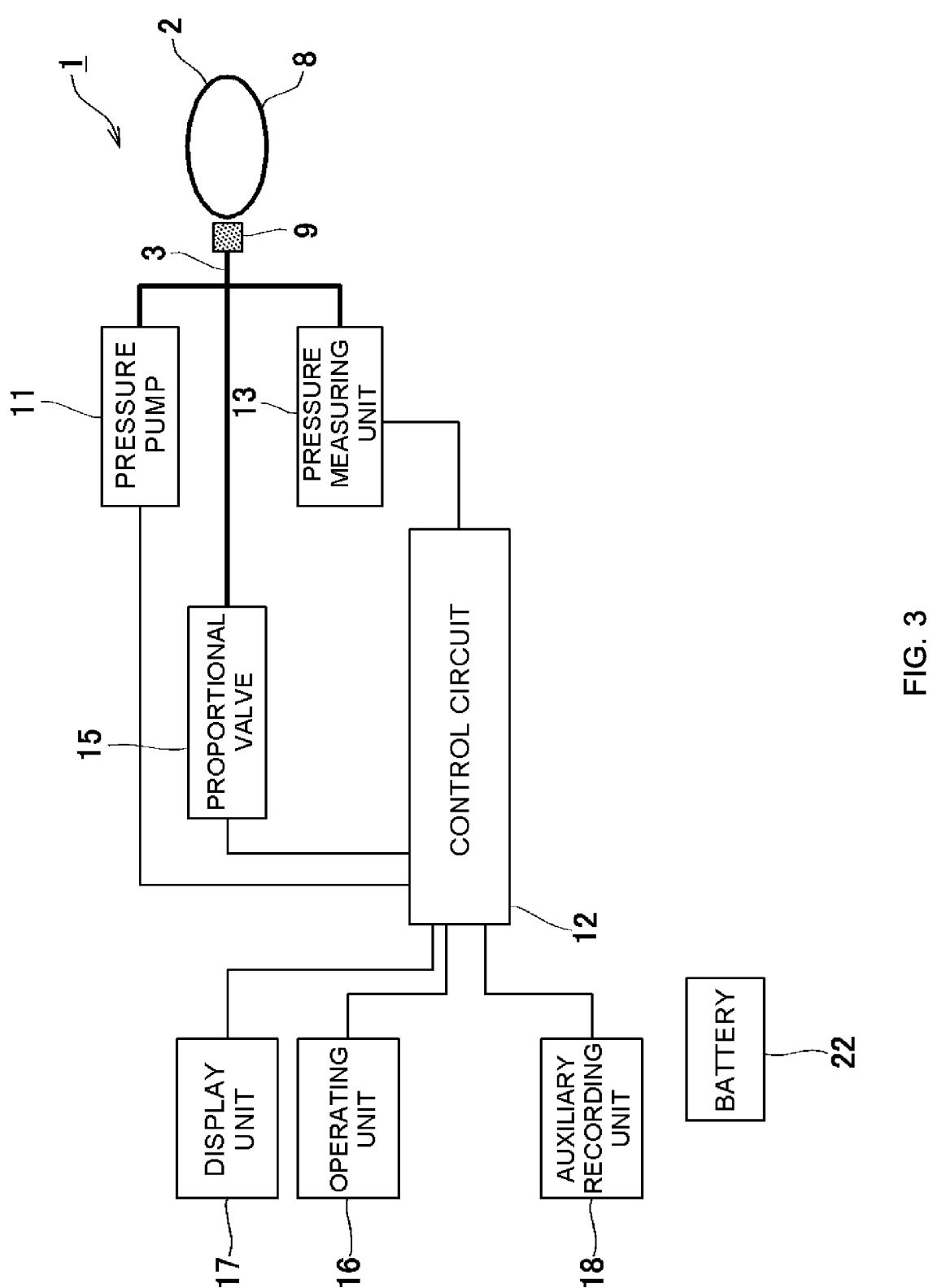
FIG. 3 is a hardware configuration diagram of a blood vessel training device included in the blood vessel training system illustrated in FIG. 1.
Figure 4:
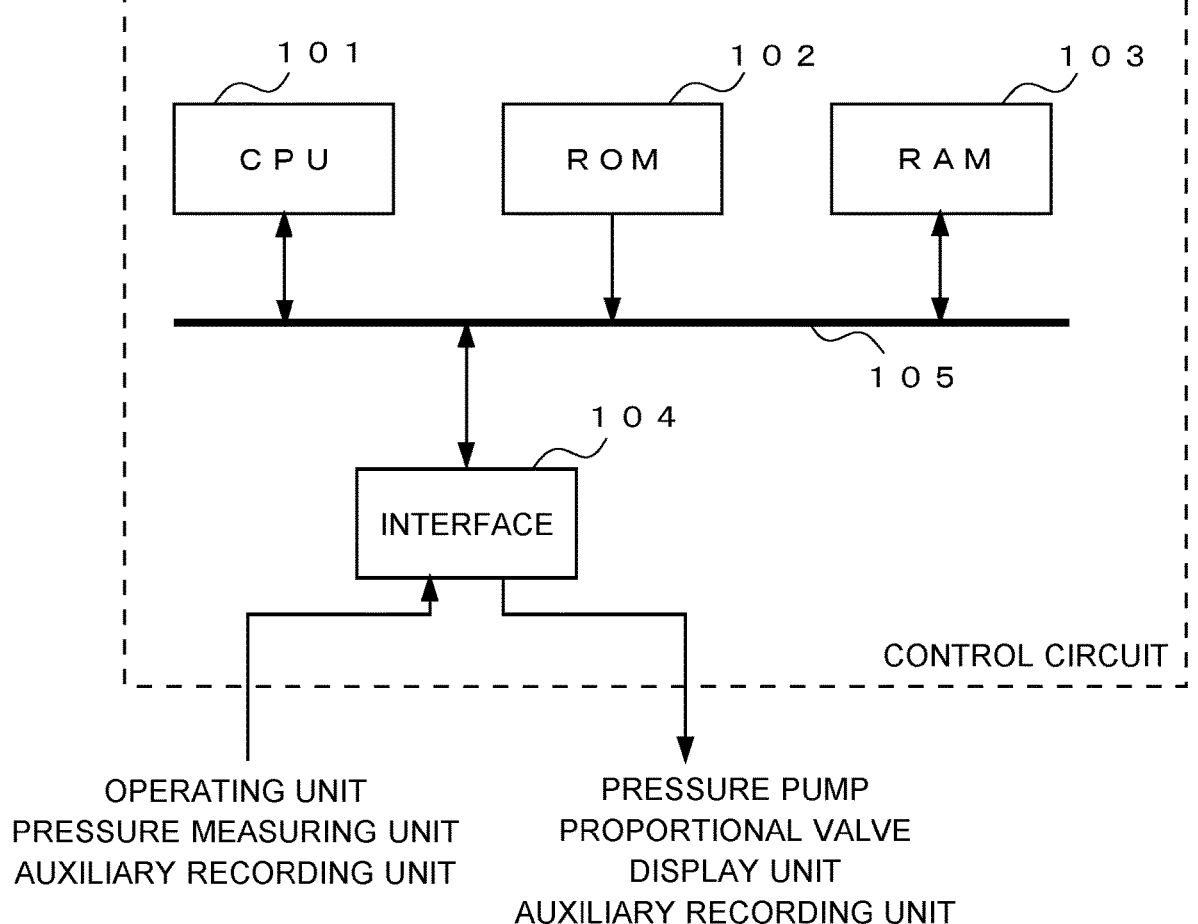
FIG. 4 for illustrating hardware

A specific configuration of the blood vessel training device 1 is illustrated in FIG. 1, FIG. 3, and FIG. 4.

The blood vessel training device 1 has a function of supplying air into the gas bladder 2X of the pressure applying belt 2 wrapped around the arm of the subject, to thereby cause the pressure applying belt 2 to tighten the arm of the subject. In this manner, the blood vessel training device 1 applies an appropriate tightening force to the arm of the subject, thereby being capable of, for example, causing occlusion of an artery of the arm and releasing the occlusion.

Further, as described later, the blood vessel training device 1 has a function of detecting a pulse wave amplitude of the arm of the subject to which the pressure applying belt 2 is attached.

Further, as described later, the blood vessel training device 1 has a function of executing pre-processing, treatment processing, post-processing, and evaluation processing.

The blood vessel training device 1 according to this embodiment is formed by, as illustrated in FIG. 1, mounting or incorporating various components to a hollow casing 1X, examples of which include a resin box, but the present embodiments are not always limited thereto.

The casing 1X of the blood vessel training device 1 has an operating unit 16 provided in an appropriate form, for example, in a form of buttons or a dial. The operating unit 16 is used for generating data by being operated. The operating unit 16 is connected to a control circuit 12 so that required data can be input to the control circuit 12. Through the operation of the operating unit 16, a processing series (evaluation-enabled mode) formed of the pre-processing, the treatment processing, the post-processing, and the evaluation processing, which are described later, can be started or ended. The blood vessel training device 1 according to this embodiment may be able to execute a processing series (evaluation-disabled mode) formed of the pre-processing and the treatment processing with an omission of the post-processing and the evaluation processing out of the above-mentioned four kinds of processing.

At least the input of data required for selecting and starting any one of the evaluation-enabled mode or the evaluation-disabled mode can be performed from the operating unit 16.

The casing 1X is provided with a display unit 17. The display unit 17 displays characters or images, and includes a display, for example, a liquid crystal display (LCD). The display unit 17 displays, for example, content input through the operation of the operating unit 16 and, in this embodiment, evaluation information being information indicating how much elasticity the blood vessel of the subject has achieved before and after the treatment, but the present embodiments are not limited thereto. It is to be understood that the display unit 17 can also display information such as which mode is being currently executed and which of the pre-processing, the treatment processing, the post-processing, and the evaluation processing is further being currently executed in the currently executed mode.

The display unit 17 performs appropriate display based on data generated by the control circuit 12, which is described later. The display unit 17 may be provided with a touch panel function. In such a manner, at least a part of the functions of the operating unit 16 can be implemented by the display unit 17. It is also possible to omit the operating unit 16 so that all the functions of the operating unit 16 may be implemented by the display unit 17 having the touch panel function.

As described above, the pressure applying belt 2 to be worn on at least one of the arms of the subject can be connected to the blood vessel training device 1 as illustrated in FIG. 3.

The pressure applying belt 2 is connected to the blood vessel training device 1, as the requirement arises, through the rubber tube 3 being a tube serving as a connecting member. The required number of rubber tubes 3 basically corresponds to the number of pressure applying belts 2, and in this embodiment, the number of pressure applying belts 2 is one, and hence only one rubber tube 3 is provided. One end of the rubber tube 3 is connected to the gas bladder 2X of the pressure applying belt 2 through the coupling tube 2Y, and another end of the rubber tube 3 is connected to the blood vessel training device 1. A publicly-known or well-known valved coupler 9 is mounted to a distal end portion of the rubber tube 3, and the gas bladder 2X of the pressure applying belt 2 is connected to the valved coupler 9.

As illustrated in FIG. 3, the blood vessel training device 1 includes a pressure pump 11. The pressure pump 11 is an air pump. The pressure pump 11 is connected to the rubber tube 3 connected to the pressure applying belt 2 as described above, and can supply air into the gas bladder 2X of the pressure applying belt 2 through the rubber tube 3 and exhaust air inside the gas bladder 2X. The pressure pump 11 may include a valve (not shown) for exhausting air inside the gas bladder 2X, and in this embodiment, the pressure pump 11 includes such a valve. In this embodiment, a gas to be injected into and exhausted from the gas bladder 2X is air, but the present embodiments are not limited thereto.

The pressure pump 11 in this embodiment is incorporated in the casing 1X. However, the pressure pump 11 may be present outside the casing 1X or outside the blood vessel training device 1 separately from the blood vessel training device 1.

The blood vessel training device 1 further includes a pressure measuring unit 13. The pressure measuring unit 13 is formed of a sensor capable of measuring a pressure of a gas. The pressure measuring unit 13 measures a pressure of air inside the rubber tube 3 to indirectly measure a pressure of the gas bladder 2X, to thereby further indirectly measure a pressure applied to the arm of the subject at that time point by the pressure applying belt 2. The pressure measuring unit 13 in this embodiment is connected to a branch tube branched from the rubber tube 3, but the present embodiments are not always limited thereto. The pressure measuring unit 13 measures a pressure of air inside the branch tube, to thereby indirectly measure the pressure of the gas (in this embodiment, air) inside the gas bladder 2X. The pressure measuring unit 13 generates pressure data being data on the measured pressure of the air.

The pressure measuring unit 13 is also connected to the control circuit 12. The pressure data generated by the pressure measuring unit 13 is transmitted to the control circuit 12. The control circuit 12 uses the pressure data to control the pressure pump 11 in a manner described later. The control circuit 12 also detects a pulse wave (pulse wave amplitude) of the subject from the pressure data in a manner described later. The pressure data is successively generated to be transmitted to the control circuit 12 substantially in real time. The pressure data can be generated, for example, several times to several tens of times per second. The number of times to generate pressure data (for example, the number of times to generate pressure data per unit time period) can be determined depending on, for example, a length of a time period required for smoothly discharging air in the pre-processing described later (time period in which a first phase, which is referred to in the present application, is executed). When that time period is short, it is supposed that the number of times to generate pressure data per second is to be increased. As the number of times to generate pressure data per second is increased, it is possible to more reliably measure the pulse wave amplitude based on variation of a pressure of the air inside the gas bladder 2X, in more detail, measure the pulse wave amplitude at a moment at which the pulse wave amplitude becomes maximum. However, in general, when the pressure data is generated about several tens of times per second, a purpose thereof can be substantially achieved, and hence it is generally not required to generate pressure data a larger number of times than that. It is also possible to change the number of times to generate pressure data per second in each of the pre-processing, the treatment processing, and the post-processing, which are described later, but in this embodiment, the number of times to generate pressure data per second is set the same in all the above-mentioned three kinds of processing, but the present embodiments are not limited thereto.

In this embodiment, the control circuit 12 measures the pulse wave amplitude of the subject, thereby serving as a pulse wave measuring device in embodiments of the present application, but the pulse wave measuring device may be present outside the casing 1X or outside the blood vessel training device 1 separately from the blood vessel training device 1. For example, a pulse wave measuring device (for example, device for measuring a pulse wave amplitude by photoplethysmogram) that measures a pulse wave at a wrist that is a portion on a further distal end side of the limb relative to the portion around which the tightening band 8 is wrapped in this embodiment is publicly known or well known for several decades. When such a pulse wave measuring device is used in this embodiment to input pulse wave amplitude data on the pulse wave amplitude from the pulse wave measuring device to the control circuit 12, the function of detecting the pulse wave amplitude in the control circuit 12 can be omitted. In this manner, in this embodiment, the pulse wave amplitude is measured in the vicinity of the portion of the limb at which the tightening band 8 is fixed or on a further distal end side of the limb relative to the portion. Further, the pulse wave amplitude can be obtained through measurement by measuring the pressure of the air inside the gas bladder 2X as described above. That is, as in a case of measuring the pulse wave amplitude by a photoplethysmogram method, a parameter to be measured is not required to be the pulse wave amplitude itself, and the pulse wave amplitude may be indirectly measured through use of another parameter.

The blood vessel training device 1 according to this embodiment further includes a proportional valve 15, which is not always required. The proportional valve 15 is a control valve capable of performing proportional adjustment on the pressure of the air inside the rubber tube 3. With the presence of the proportional valve 15, even when, for example, the subject moves to cause variation in thickness of muscle of the arm to which the pressure applying belt 2 is attached, a pressure force applied to the pressure applying belt 2 is kept within a predetermined range through proportional-integral-differential (PID) control. The proportional valve 15 in this embodiment is connected to a branch tube branched from a proximal end side of the rubber tube 3, which is further different from the branch tube connected to the pressure measuring unit 13, so as to adjust the pressure of the air inside this branch tube, but the present embodiments are not always limited thereto. The proportional valve 15 is connected to the control circuit 12, and an operation of the proportional valve 15 is controlled based on data from the control circuit 12. However, the proportional valve 15 may be regarded as a part of the pressure pump 11. For example, the proportional valve 15 may play a role of discharging air from the gas bladder 2X. In that case, the pressure of the air inside the gas bladder 2X is controlled through cooperation by the pressure pump 11 for increasing the pressure and the proportional valve 15 for decreasing the pressure.

The control circuit 12 included in the blood vessel training device 1 is a computer, and governs the control of the entire blood vessel training device 1. For example, the control circuit 12 controls drive of the pressure pump 11 (and the proportional valve 15). The control circuit 12 also evaluates the elasticity of the blood vessel of the subject in a manner described later.

The control circuit 12 of the blood vessel training device 1 includes hardware components illustrated in FIG. 4. The hardware components included in the control circuit 12 are a CPU 101 that is an arithmetic unit, a ROM 102 having recorded therein a program for determining processing to be executed by the CPU 101 and data required for executing programs, a RAM 103 that provides a work space for the CPU 101 to execute the programs, and an interface 104 that connects an external device and the CPU 101 and the like. Further, the CPU 101, the ROM 102, the RAM 103, and the interface 104 are connected to each other through a bus 105. The programs and data contained in the ROM 102 include at least a computer program and data that are required for generating functional blocks described later inside the control circuit 12. This computer may generate functional blocks described later alone, or may generate functional blocks in cooperation with an OS or another program. Various types of data are recorded on the RAM 103, but a function of the RAM 103 may be implemented by an auxiliary recording unit 18 described later, or a function of the auxiliary recording unit 18 may be implemented by the RAM 103. Further, the control circuit 12 may include a large-capacity recording medium such as a hard disk drive (HDD), and the large-capacity recording medium may implement at least a part of functions of the ROM 102 and the RAM 103. The interface 104 is connected to the pressure measuring unit 13, the pressure pump 11, the proportional valve 15, the operating unit 16, the display unit 17, and the auxiliary recording unit 18.

Figure 5:
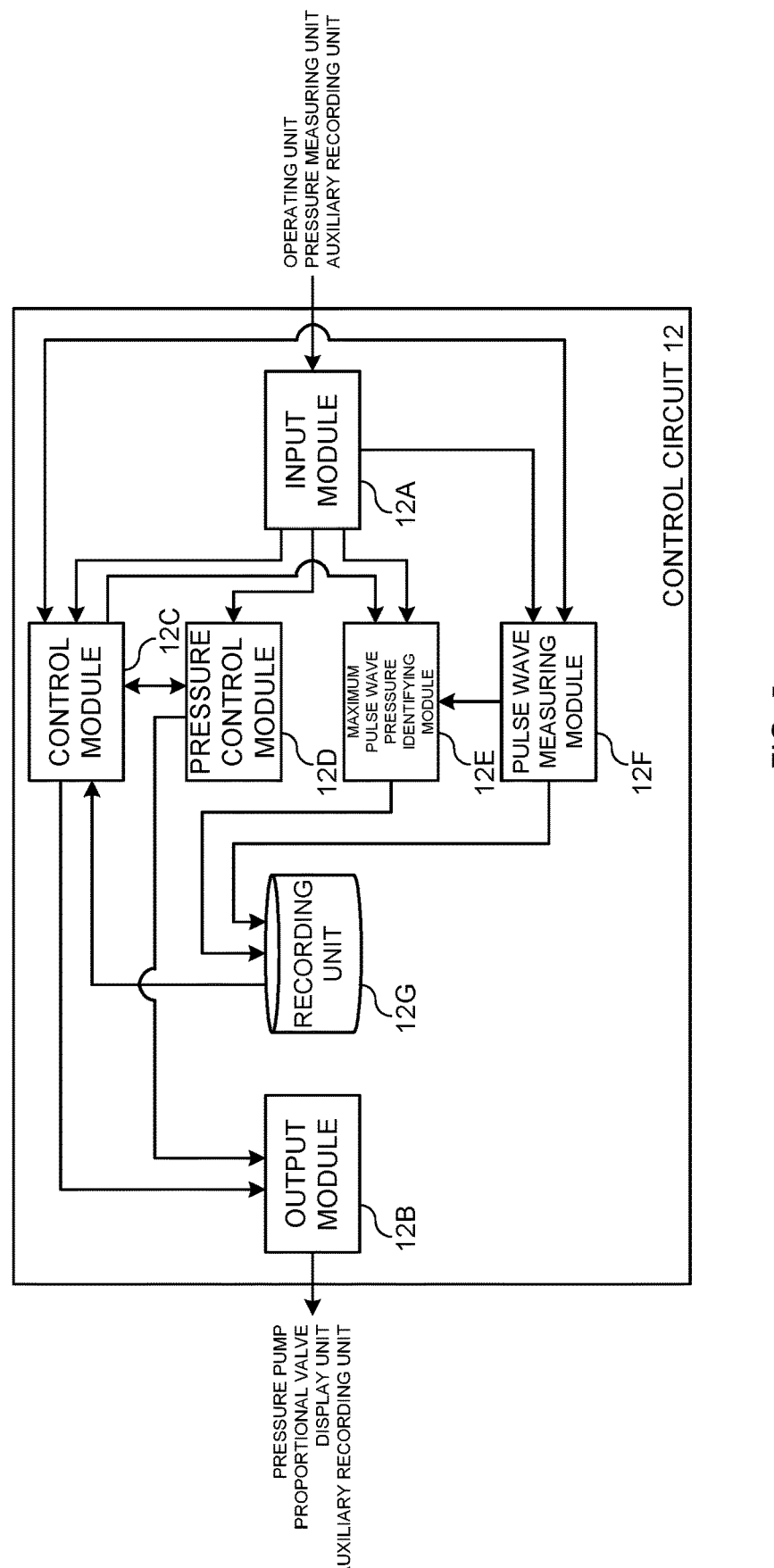
FIG. 5 is a block diagram for illustrating functional blocks formed inside the control circuit.

Through execution of the above-mentioned program, functional blocks as illustrated in FIG. 5 are generated in the control circuit 12.

The functional blocks to be generated are an input module 12A, an output module 12B, a control module 12C, a pressure control module 12D, a maximum pulse wave pressure identifying module 12E, a pulse wave measuring module 12F, and a recording unit 12G. The functional blocks that perform some kind of information processing other than the recording unit 12G, for example, the control module 12C, the pressure control module 12D, the maximum pulse wave pressure identifying module 12E, and the pulse wave measuring module 12F are implemented by the CPU 101 described above, or each kind of processing executed by each thereof is achieved by processing executed by the CPU 101.

The input module 12A receives input of data from the outside to the control circuit 12. The input module 12A transmits the received data to an appropriate functional block. For example, the input module 12A receives data input from the operating unit 16, and transmits the data to the control module 12C. The input module 12A also receives the pressure data from the pressure measuring unit 13, and transmits the pressure data to the pressure control module 12D, the maximum pulse wave pressure identifying module 12E, and the pulse wave measuring module 12F.

In some cases, the auxiliary recording unit 18, which is described later, transmits pre-maximum pulse wave amplitude data, post-maximum pulse wave amplitude data, and maximum pulse wave pressure data, which are also described later, to the input module 12A. The input module 12A that has received those pieces of data transmits the received pre-maximum pulse wave amplitude data, post-maximum pulse wave amplitude data, or maximum pulse wave pressure data to the control module 12C.

The control module 12C is a module that controls the entire blood vessel training device 1. The control module 12C performs such control based on the data input from the operating unit 16. The control to be performed by the control module 12C includes, for example, processing for switching between on and off of a power of the blood vessel training device 1, starting and ending the evaluation-enabled mode and the evaluation-disabled mode, and starting and ending the pre-processing, the treatment processing, the post-processing, and the evaluation processing (among which the post-processing and the evaluation processing are omitted in a case of the evaluation-disabled mode), which are described later, when each of those modes is being executed. When n the control module 12C is to start the evaluation-enabled mode or the evaluation-disabled mode, the control module 12C transmits data to that effect to the pressure control module 12D and the pulse wave measuring module 12F.

Further, when the control module 12C is to execute each of the pre-processing, the treatment processing, and the post-processing, the control module 12C transmits, to the pressure control module 12D, pressure control data being data of a mathematical function (or timing chart) of time and pressure, which indicates how an air pressure inside the gas bladder 2X is to be maintained when each of the pre-processing, the treatment processing, and the post-processing is performed. The pressure control data may be recorded in a functional block (not shown) for recording data included in the control module 12C, but may be recorded in the auxiliary recording unit 18 described above. In this case, the control module 12C reads out the pressure control data recorded in the auxiliary recording unit 18, as the requirement arises, and transmits the pressure control data to the pressure control module 12D.

The control module 12C has a function of generating part of the pressure control data to be used when the pre-processing is executed and the pressure control data to be used when the treatment processing and the post-processing are executed. The generated pressure control data may be temporarily transmitted to the auxiliary recording unit 18 through the output module 12B and, as the requirement arises, read out by the control module 12C to be then transmitted to the pressure control module 12D, or may be transmitted to the pressure control module 12D at a stage at which the pressure control data is generated. In a case of generating part of the pressure control data to be used when the pre-processing is executed and the pressure control data to be used when the treatment processing and the post-processing are executed, the control module 12C uses the maximum pulse wave pressure data being data specifying the maximum pulse wave pressure (described later). In this embodiment, the maximum pulse wave pressure data is recorded in the recording unit 12G, and hence the control module 12C reads out the maximum pulse wave pressure data from the recording unit 12G, as the requirement arises.

Further, as described later, when each of the pre-processing and the post-processing is being executed, in some cases, the control module 12C receives, from the pulse wave measuring module 12F, pulse wave data being data specifying the pulse wave amplitude. The control module 12C that has received the pulse wave data transmits the pulse wave data to the output module 12B.

There are also cases in which the control module 12C receives, from the recording unit 12G, a pair of the pre-maximum pulse wave amplitude data and the post-maximum pulse wave amplitude data. The control module 12C has a function of generating, upon reception of those two kinds of data, evaluation data indicating an evaluation result of the elasticity of the blood vessel of the subject based on those two kinds of data. After having generated the evaluation data, the control module 12C transmits the evaluation data to the output module 12B.

The pressure control module 12D is a module that controls the pressure pump 11 to control the pressure of the air inside the gas bladder 2X provided to the pressure applying belt 2, to thereby control the pressure to be applied to the arm of the subject by the pressure applying belt 2. The above-mentioned function is exerted when any one of the pre-processing, the treatment processing, or the post-processing is executed. The control of the pressure of the air inside the gas bladder 2X of the pressure applying belt 2 in each of the pre-processing, the treatment processing, and the post-processing is carried out in accordance with the pressure control data received from the control module 12C by the pressure control module 12D before each of those three kinds of processing is executed.

The pressure control module 12D receives the pressure data from the input module 12A as described above, and uses the received pressure data to monitor, substantially in real time, the pressure of the air inside the gas bladder 2X provided to the pressure applying belt 2 at that time point. The pressure control module 12D includes a timer (not shown), and generates first control data being data for driving the pressure pump 11 so as to keep the pressure of the air inside the gas bladder 2X at a time point specified by the timer at a pressure specified by the above-mentioned pressure control data. When the pressure pump 11 receives the first control data, the pressure pump 11 is driven in accordance with the first control data, and the pressure of the air inside the gas bladder 2X is changed or maintained as appropriate.

The pressure control module 12D also generates second control data for controlling the proportional valve 15 described later. The proportional valve 15 that has received the second control data in a manner described later is driven as described later in accordance with an instruction based on the second control data. The pressure control module 12D transmits the first control data and the second control data that have been generated to the output module 12B. Details of how to generate the first control data and the second control data are described later. When there is no proportional valve 15, it is to be understood that the pressure control module 12D is not required to have the function of generating the second control data.

The pulse wave measuring module 12F receives the pressure data from the input module 12A. The pressure data reaches the pulse wave measuring module 12F substantially in real time when the pressure data is generated. The pressure data is transmitted from the pressure measuring unit 13 to the pulse wave measuring module 12F when each of the pre-processing and the post-processing is being executed. The pulse wave measuring module 12F can detect the pulse wave amplitude of the subject superimposed on the pressure data after performing publicly-known or well-known processing, for example, removing noise from the pressure data, and further detect, from the detected pulse wave amplitude, a timing at which the pulse wave amplitude became maximum and the pulse wave amplitude at that time point. The pulse wave amplitude that became maximum when the pre-processing was being executed is a pre-maximum pulse wave amplitude, and the pulse wave amplitude that became maximum when the post-processing was being executed is a post-maximum pulse wave amplitude. The pre-maximum pulse wave amplitude data, which is data specifying the pulse wave amplitude of the pre-maximum pulse wave amplitude that occurred while the pre-processing was being executed, and the post-maximum pulse wave amplitude data, which is data specifying the pulse wave amplitude of the post-maximum pulse wave amplitude that occurred while the post-processing was being executed, are generated at, for example, a time point at which the pre-processing has been ended and a time point at which the post-processing has been ended, and are transmitted from the pulse wave measuring module 12F to the recording unit 12G. In this manner, the recording unit 12G records the pre-maximum pulse wave amplitude data and the post-maximum pulse wave amplitude data.

Further, timing data, which is data indicating a timing at which the pulse wave amplitude became maximum in the pre-processing, is transmitted from the pulse wave measuring module 12F to the maximum pulse wave pressure identifying module 12E. In this embodiment, even when start pressure determination processing, which is described later, is executed, the pulse wave measuring module 12F detects the timing at which the pulse wave amplitude became maximum and the pulse wave amplitude at that time point, and transmits the pulse wave data specifying the maximum pulse wave amplitude to the control module 12C.

The maximum pulse wave pressure identifying module 12E has a function of generating, when the pre-processing is being executed, maximum pulse wave pressure data being the data specifying the maximum pulse wave pressure being the pressure of the air inside the gas bladder 2X at a time at which the pre-maximum pulse wave amplitude occurred. The maximum pulse wave pressure identifying module 12E functions, that is, identifies the maximum pulse wave pressure when the pre-processing is being executed. As described above, the maximum pulse wave pressure identifying module 12E receives the pressure data from the input module 12A. In the same manner as the pulse wave measuring module 12F, the maximum pulse wave pressure identifying module 12E receives the pressure data generated by the pressure measuring unit 13 substantially in real time after the pressure data is generated. In the same manner as the pressure control module 12D, the maximum pulse wave pressure identifying module 12E monitors the pressure of the air inside the gas bladder 2X based on the pressure data. Meanwhile, as described above, the maximum pulse wave pressure identifying module 12E receives the timing data from the pulse wave measuring module 12F. The maximum pulse wave pressure identifying module 12E identifies the pressure of the air inside the gas bladder 2X at the timing specified by the timing data as the maximum pulse wave pressure being the pressure of the air inside the gas bladder 2X at the time at which the pulse wave amplitude became maximum, in other words, at the time at which the pre-maximum pulse wave amplitude occurred. After having identified the maximum pulse wave pressure, the maximum pulse wave pressure identifying module 12E generates maximum pulse wave pressure data indicating the maximum pulse wave pressure, and transmits the maximum pulse wave pressure data to the recording unit 12G.

The recording unit 12G is a recording medium for recording data, and is implemented by, for example, the RAM 103 in this embodiment. The data recorded in the recording unit 12G includes at least the pre-maximum pulse wave amplitude data, the post-maximum pulse wave amplitude data, and the maximum pulse wave pressure data.

The output module 12B outputs data from the control circuit 12 to the outside. The output module 12B transmits the received data to an appropriate device outside the control circuit 12.

As described above, in some cases, the output module 12B receives the evaluation data indicating the evaluation result regarding the elasticity of the blood vessel of the subject from the control module 12C. The output module 12B has a function of generating, upon reception of this evaluation data, image data on an image including, for example, characters for use to display the evaluation data on the display unit 17. The generated image data is transmitted from the output module 12B to the display unit 17. The display unit 17 that has received the image data displays the image based on the image data.

There are also cases in which the output module 12B receives the first control data and the second control data from the pressure control module 12D. When receiving the first control data, the output module 12B transmits the first control data to the pressure pump 11, and when receiving the second control data, the output module 12B transmits the second control data to the proportional valve 15. The pressure pump 11 that has received the first control data is driven in accordance with the first control data, and the proportional valve 15 that has received the second control data is driven in accordance with the second control data.

As described above, there are also cases in which the output module 12B receives the pressure control data from the control module 12C. When the output module 12B receives the pressure control data, the output module 12B transmits the pressure control data to the auxiliary recording unit 18. The auxiliary recording unit 18 is, for example, a part of the RAM 103, and has a function of recording data, and at least the pressure control data is recorded in the auxiliary recording unit 18. In the auxiliary recording unit 18, other data, for example, appropriate data such as a history of operations performed on the operating unit 16 and a history of occurrence of abnormality may be recorded.

Further, the blood vessel training device 1 is mounted with a battery 22 for driving the control circuit 12, the pressure measuring unit 13, the proportional valve 15, the operating unit 16, the display unit 17, the auxiliary recording unit 18, and the like that form the blood vessel training device 1. The battery 22 may be a publicly-known or well-known battery, and a function, a use method, and the like of the battery 22 in this embodiment are also publicly known or well known. Thus, detailed description thereof is omitted.

Next, a method of using this blood vessel training system and operations thereof is described.

First, a doctor, a trainer, or another practitioner operates a power switch included in the operating unit 16 of the blood vessel training device 1 to turn on the power and activate the blood vessel training device 1. Data input through the operating unit 16 is transmitted to the control module 12C through the interface 104 and the input module 12A. The control module 12C that has received this data turns on the power of the blood vessel training device 1.

Around a time at which the power of the blood vessel training device 1 is turned on, the practitioner fixes the pressure applying belt 2 at a predetermined position in the vicinity of a proximal end of one of the arms of the subject. When the pressure applying belt 2 is to be fixed, the gas bladder 2X is brought into abutment against the arm. The pressure applying belt 2 is wrapped around the arm from the lower side of FIG. 2, and the fixing portion 22 is fixed to an outer-side surface of the tightening band 8, to thereby removably fix the pressure applying belt 2 to the arm of the subject. However, under this state, the pressure applying belt 2 is considerably loosely attached to the arm. Under such a state, the pressure applying belt 2 is connected to the blood vessel training device 1 through the tube 3. Through this connection, the pressure of the air inside the gas bladder 2X of the pressure applying belt 2 can be controlled by the blood vessel training device 1.

After that, in order to perform the blood vessel training and to evaluate to what extent the elasticity of the blood vessel of the subject has increased, the pre-processing, the treatment processing, and the post-processing are sequentially executed in the stated order, but preliminary processing is executed prior to the pre-processing. However, the preliminary processing is not always required.

Briefly speaking, the preliminary processing is processing for adjusting a wearing pressure to be applied to the arm of the subject by the pressure applying belt 2, which is described later, to an appropriate magnitude.

When the preliminary processing is to be executed, the practitioner operates the operating unit 16 to input data indicating that the preliminary processing is to be executed. This data is transmitted from the operating unit 16 to the control module 12C through the interface 104 and the input module 12A. The control module 12C that has received the data reads out, from the auxiliary recording unit 18, the data indicating that the preliminary processing is to be executed and the pressure control data being data of a mathematical function of time and pressure, which indicates how the air pressure inside the gas bladder 2X is to be maintained when the preliminary processing is performed. This pressure control data is not generated by the control module 12C, and is continuously recorded in the auxiliary recording unit 18 from the beginning. The pressure control data is read out from the auxiliary recording unit 18, reaches the control module 12C through the interface 104 and the input module 12A, and is transmitted from the control module 12C to the pressure control module 12D.

The pressure control module 12D generates first control data so that the pressure of the air inside the gas bladder 2X of the pressure applying belt 2 is as designated by the received pressure control data. The generated first control data is transmitted to the pressure pump 11 through the output module 12B, and the pressure pump 11 is driven. Under the control of the first control data, the pressure pump 11 supplies air to the gas bladder 2X of the pressure applying belt 2, and first sets the pressure of the air inside the gas bladder 2X to a relatively low pressure of, in general, about 10 mmHg to about 15 mmHg, for example, about 13 mmHg. At this time, a small tightening force applied to the arm by the pressure applying belt 2 is useful for preventing the pressure applying belt 2 from rotating around the arm.

In this embodiment, the pressure control data transmitted from the control module 12C to the pressure control module 12D is an instruction "to increase the pressure of the air inside the gas bladder 2X to about 13 mmHg within several seconds after the preliminary processing is started." Once the pressure of the air inside the gas bladder 2X has increased to about 13 mmHg, an amount of the air inside the gas bladder 2X in this embodiment is maintained as it is. That is, after the pressure of the air inside the gas bladder 2X has reached 13 mmHg, the pressure pump 11 stops being driven until the preliminary processing is ended.

Processing for increasing the pressure of the air inside the gas bladder 2X to 13 mmHg is performed as follows. Briefly speaking, the pressure control module 12D causes the pressure pump 11 to perform any one of operations for injecting air into the gas bladder 2X, exhausting air therefrom, and stopping both kinds of processing for injecting and exhausting air, while monitoring, substantially in real time, the pressure of the air inside the gas bladder 2X provided to the pressure applying belt 2. The pressure measuring unit 13 continuously generates, at a predetermined time interval (in this embodiment, for example, time interval such as several times to several tens of times per second), pressure data indicating the pressure of the air inside the gas bladder 2X at that time point, and continuously transmits the generated pressure data to the pressure control module 12D through the interface 104 and the input module 12A. The pressure control module 12D can grasp the pressure of the air inside the gas bladder 2X at that time point based on the received pressure data. When the pressure data falls below 13 mmHg, the pressure control module 12D generates first control data indicating that the air is to be supplied into the gas bladder 2X, and transmits the first control data to the pressure pump 11 through the output module 12B and the interface 104. Thus, the pressure pump 11 supplies air into the gas bladder 2X, and hence the pressure of the air inside the gas bladder 2X increases. As this processing continues, the pressure of the air inside the gas bladder 2X keeps increasing. When the pressure of the air inside the gas bladder 2X indicated by the pressure data generated by the pressure measuring unit 13 indicates 13 mmHg, the pressure control module 12D generates first control data indicating that the pressure pump 11 is to be stopped, and transmits the first control data to the pressure pump 11. Thus, the pressure pump 11 is stopped. When the pressure of the air inside the gas bladder 2X indicated by the pressure data generated by the pressure measuring unit 13 happens to indicate a numerical value exceeding 13 mmHg, the pressure control module 12D generates first control data indicating that an operation for discharging air inside the gas bladder 2X is to be performed by the pressure pump 11, and transmits the first control data to the pressure pump 11. Thus, the pressure pump 11 discharges the air inside the gas bladder 2X by, for example, opening the valve (not shown), and hence the pressure of the air inside the gas bladder 2X decreases. In this manner, the pressure control module 12D causes the pressure of the air inside the gas bladder 2X to reach 13 mmHg and to be maintained at 13 mmHg. Processing for discharging the air inside the gas bladder 2X may be performed by the proportional valve 15 instead of the pressure pump 11. Such a method of controlling the pressure by the pressure control module 12D is the same in any one of cases of the pre-processing, the treatment processing, and the post-processing.

Under the above-mentioned state, the practitioner adjusts a degree to which the arm is tightened by the pressure applying belt 2 worn on a predetermined portion of the subject, to thereby adjust the pressure force applied to the arm of the subject by the pressure applying belt 2 to become a predetermined tightening force of, for example, about 40 mmHg, which includes the above-mentioned air pressure of 13 mmHg. At this time, a wearing pressure applied to the arm by the pressure applying belt 2 excluding the tightening force based on the pressure of the air inside the gas bladder 2X is about 27 mmHg in this case. The above-mentioned pressure of 13 mmHg adjusted in this manner is a wearing pressure. The wearing pressure is an initial pressure applied to the arm of the subject by the pressure applying belt 2, and serves as a so-called zero point of a pressure to be applied to the arm of the subject by the pressure applying belt 2 due to the variation of the pressure of the air inside the gas bladder 2X thereafter. The wearing pressure is not required to be set to about 13 mmHg, and may be set larger or set smaller. When the subject is in a posture with no fear of dropping the pressure applying belt 2 from the arm of the subject, for example, the subject is in a supine position and extends his or her arm on the floor, the wearing pressure may be 0 mmHg.

The wearing pressure at the current time point can be confirmed, for example, as follows. As described above, in this embodiment, the pressure measuring unit 13 continuously transmits the pressure data to the pressure control module 12D. This enables the pressure control module 12D to always grasp the pressure of the air inside the gas bladder 2X at that time point. In addition, in this embodiment, the pressure control module 12D continuously transmits, to the control module 12C, the data indicating the pressure of the air inside the gas bladder 2X at that time point, which has been grasped based on the pressure data. This processing may be achieved as processing for transferring, by the pressure control module 12D, the pressure data received from the pressure measuring unit 13 to the control module 12C. In any case, in the same manner as the pressure control module 12D, the control module 12C can grasp the pressure of the air inside the gas bladder 2X. The control module 12C that has received that data generates data specifying a numerical value indicating the pressure of the air inside the gas bladder 2X at that time point, and transmits the data to the output module 12B. The output module 12B generates image data for displaying the numerical value on the display unit 17, and transmits the image data to the display unit 17 through the interface 104. On the display unit 17 that has received the image data, the image based on the image data is displayed. In the above-mentioned manner, when the preliminary processing is being executed, the display unit 17 continuously displays the pressure of the air inside the gas bladder 2X substantially in real time. The practitioner adjusts the tightening degree of the pressure applying belt 2 so that the pressure of the air inside the gas bladder 2X at that time point, which is displayed on the display unit 17, becomes an appropriate value, in this embodiment, 40 mmHg, to which the present embodiments are not limited. As described above, after the pressure of the air inside the gas bladder 2X has been increased to 13 mmHg, the pressure pump 11 stops being driven under that state. Therefore, when the pressure applying belt 2 is tightened, the pressure of the air inside the gas bladder 2X squeezed between the tightening band 8 and the arm increases, while the pressure of the air inside the gas bladder 2X decreases when the pressure applying belt 2 is loosened. While viewing the numerical value displayed on the display unit 17, which changes depending on the tightening degree of the pressure applying belt 2, the practitioner adjusts the tightening degree of the pressure applying belt 2.

After the adjustment of the tightening degree of the pressure applying belt 2 is ended, the practitioner operates the operating unit 16 to end the preliminary processing. Data indicating that the preliminary processing is to be ended is transmitted to the control module 12C in the same manner as the data transmitted when the preliminary processing is to be executed. The control module 12C transmits an instruction to end the preliminary processing to the pressure control module 12D. The pressure control module 12D that has received the instruction generates first control data indicating that the air inside the gas bladder 2X is to be discharged until the pressure of the air inside the gas bladder 2X becomes, for example, a normal pressure, and transmits the first control data to the pressure pump 11. The pressure pump 11 that has received the first control data discharges the air inside the gas bladder 2X. Thus, the preliminary processing is ended.

Under the above-mentioned state, the practitioner performs an operation for starting any one of the evaluation-enabled mode or the evaluation-disabled mode on the operating unit 16. The evaluation-disabled mode differs from the evaluation-enabled mode only in that the post-processing and the evaluation processing, which are described later, in the evaluation-enabled mode are eliminated, that is, the evaluation-disabled mode is ended at a time point at which the treatment processing, which is described later, has been ended. Thus, the following description is given on the assumption that execution of the evaluation-enabled mode has been selected.

When the evaluation-enabled mode is to be executed, the practitioner operates the operating unit 16 to input data indicating that the evaluation-enabled mode is to be executed. This data is transmitted from the operating unit 16 to the control module 12C through the interface 104 and the input module 12A.

After that, the control module 12C in this embodiment automatically executes the pre-processing, the treatment processing, the post-processing, and the evaluation processing in order. However, the evaluation processing is not required to be sequentially executed after the post-processing. The evaluation processing may be executed after a time period from the end of the post-processing, for example, when the operator operates the operating unit 16.

The control module 12C that has received the data indicating that the evaluation-enabled mode is to be executed transmits data indicating that the former stage part of the pre-processing in the evaluation-enabled mode is to be executed to the pressure control module 12D and the pulse wave measuring module 12F. Further, the control module 12C reads out, from the auxiliary recording unit 18, the pressure control data being the data of the mathematical function of time and pressure, which indicates how the air pressure inside the gas bladder 2X is to be maintained, when the start pressure determination processing described later, which is processing in the former stage of the pre-processing, is executed. This pressure control data is also not generated by the control module 12C, and is continuously recorded in the auxiliary recording unit 18 from the beginning. The pressure control data is read out from the auxiliary recording unit 18 and transmitted from the control module 12C to the pressure control module 12D in the same manner as in a case of the preliminary processing.

Thus, the start pressure determination processing being a part of the pre-processing is started, and is performed as follows. As is the same with the post-processing, the subject maintains a resting state while the pre-processing including the start pressure determination processing is being executed.

The start pressure determination processing is processing for determining an initial value of the pressure of the air inside the gas bladder 2X to be used when the latter stage of the pre-processing described later is started.

Figure 6:
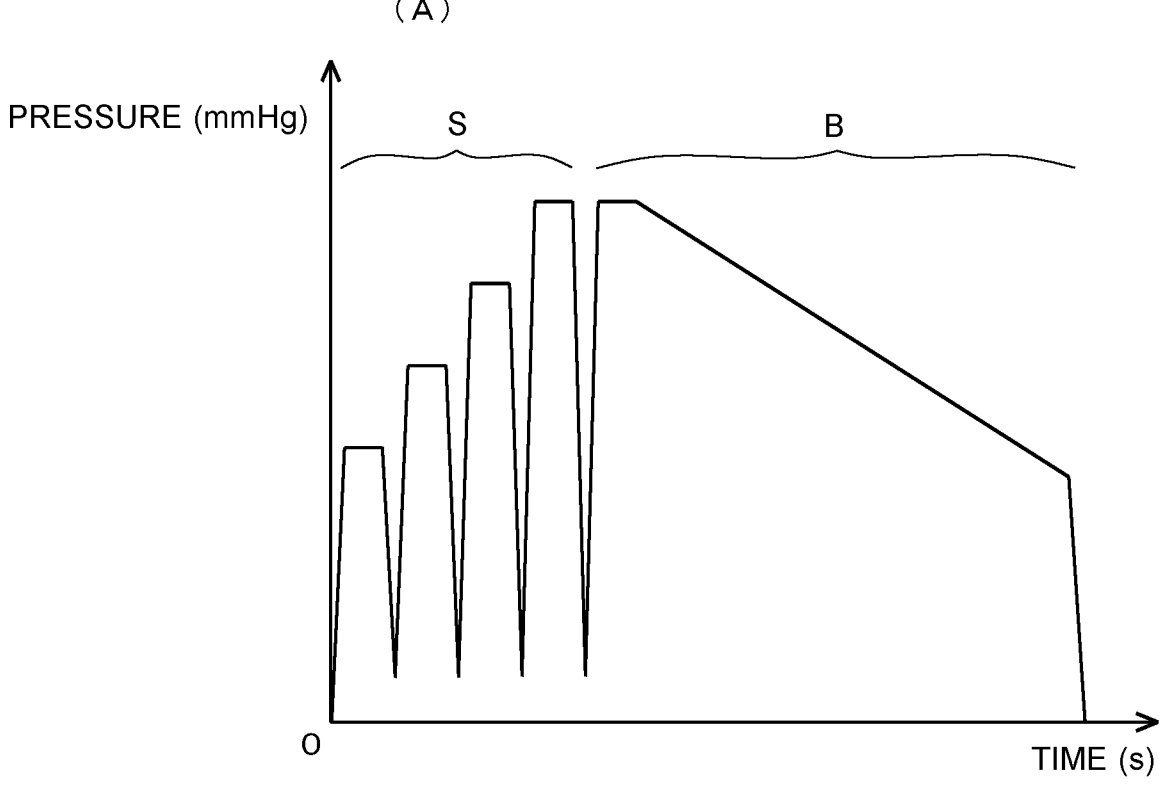
FIG. 6 are timing charts for illustrating a pressure of air inside a gas bladder at a time at which pre-processing is executed in the blood vessel training system illustrated in FIG. 1.
Figure 6:
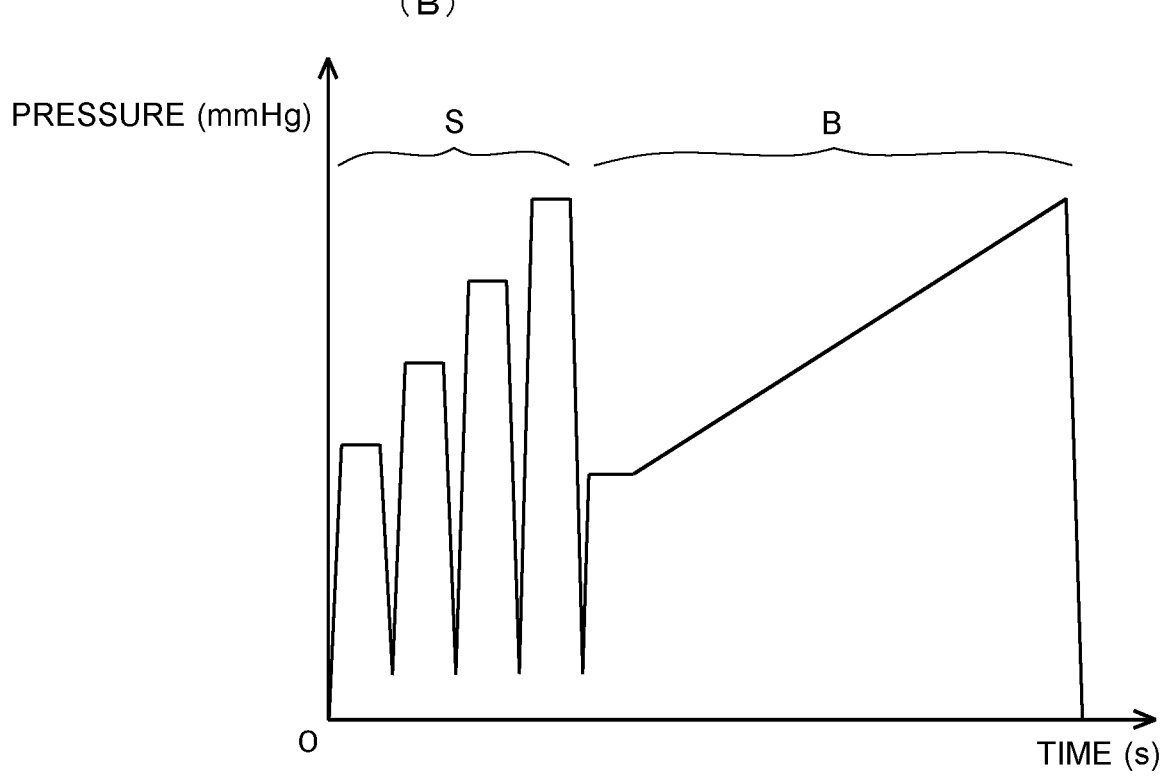

In FIG. 6(A), a timing chart of the pre-processing is illustrated. In FIG. 6(A), the horizontal axis represents a lapse of time from a time point at which the start pressure determination processing is started, and the vertical axis represents the pressure of the air inside the gas bladder 2X of the pressure applying belt 2. In the timing chart of FIG. 6(A), the part denoted by reference symbol "S" represents a time slot in which the start pressure determination processing is being executed.

In the start pressure determination processing in this embodiment, the pressure of the air inside the gas bladder 2X of the pressure applying belt 2 is gradually increased stepwise as illustrated in FIG. 6(A). Changing the pressure of the air of the gas bladder 2X over time in this manner (gradually increasing the pressure stepwise) is the content of the pressure control data in the start pressure determination processing, which has been generated by the control module 12C and transmitted to the pressure control module 12D. However, the pressure control data at a time of the start pressure determination processing in this embodiment does not specify to which stage the pressure of the air inside the gas bladder 2X is to be increased. This point is described later.

The pressure of the air inside the gas bladder 2X is, for example, 0 mmHg at a first time point of the start pressure determination processing, and is increased to a predetermined pressure in several seconds, thereby performing pressure application in a first stage. The pressure of the air inside the gas bladder 2X at that time can be set to a pressure that is smaller by some extent, for example, by about 30 mmHg than a pressure that is thought to cause no tension to a vascular wall of the artery of the subject. As has been described above, no tension is applied to the vascular wall of the artery of the subject when a pressure around a mean blood pressure of the subject is applied to the arm of the subject. Therefore, for example, the blood pressure of the subject can be measured in advance, and a pressure smaller than the mean blood pressure of the subject by some extent can be set as the pressure in the first stage described above. When input of data on the mean blood pressure of the subject is allowed to be performed from the operating unit 16, the control module 12C that has received the data can also determine the pressure in the first stage depending on the mean blood pressure of the subject, and generate pressure control data at the time of the start pressure determination processing in consideration thereof. In this case as well, the pressure control data can be temporarily recorded in the auxiliary recording unit 18, and, as the requirement arises, read out by the control module 12C. The pressure in the pressure application in the first stage can be determined based on knowledge, experience, or the like of the practitioner irrespective of the mean blood pressure of the subject, or can be fixedly set as a pressure smaller by about 30 mmHg than a possible average blood pressure.

The pressure application in the first stage is continued at the same pressure for a predetermined time period, for example, 10 seconds. After that, the pressure application in the first stage is ended, and the pressure of the air inside the gas bladder 2X is dropped to a relatively small pressure, for example, 15 mmHg in several seconds. As is the same with the following, after the pressure application in each stage is completed, the pressure of the air inside the gas bladder 2X may be dropped to 0 mmHg. Subsequently, pressure application in a second stage is performed. The pressure application in the second stage is performed immediately after the pressure application in the first stage is performed, and the pressure of the air inside the gas bladder 2X, which has been 15 mmHg, is increased to a predetermined pressure in several seconds. The pressure of the air inside the gas bladder 2X in the second stage is set larger than the pressure of the air inside the gas bladder 2X in the first stage by some extent, for example, by about 10 mmHg. The pressure application in the second stage is continued at the same pressure for a predetermined time period, in general, 10 seconds, which is the same as in a case of the pressure application in first stage. After that, the pressure application in the second stage is ended. In the same manner, pressure application in a third stage, pressure application in a fourth stage, . . . are repeatedly executed a required number of times. Description of the "required number of times" is given later.

As described above, an internal pressure (outward pressure) caused by the blood pressure is applied to the vascular wall of the artery of the subject. Meanwhile, when a pressure is applied to the arm from the outer side, the pressure acts on the vascular wall of the artery as an external pressure (inward pressure). When the internal pressure and the external pressure are balanced, there is achieved a state in which no tension is applied to the vascular wall. While pulse waves are caused in the artery by a heartbeat, the pulse wave amplitude becomes maximum when no tension is applied to the vascular wall, and decreases irrespective of whether the internal pressure is larger or smaller than that. Roughly speaking, when the pressure applied to the arm by the pressure applying belt 2 is plotted on the horizontal axis and the pulse wave amplitude is plotted on the vertical axis, the pulse wave amplitude draws an upwardly convex parabola that has an apex when the pressure applied to the arm by the pressure applying belt 2 becomes a magnitude balanced with the internal pressure applied to the vascular wall.

When the pressure of the air inside the gas bladder 2X is increased stepwise as described above, the pressure applied to the arm by the pressure applying belt 2 eventually exceeds the internal pressure applied to the vascular wall. Finding out such a pressure is a purpose of the start pressure determination processing.

While the start pressure determination processing is being executed, the pressure data is constantly repeatedly input to the pulse wave measuring module 12F as described above. Therefore, the pulse wave measuring module 12F is in a state of constantly monitoring the pulse wave amplitude at that time point. The pressure data contains, in addition to data on a large change in air pressure caused by the injection or exhaust of air to or from the gas bladder 2X by the pressure pump 11, data on extremely minute variation in air pressure caused by the pulse wave amplitude of the pulse wave of the subject. The pulse wave measuring module 12F that has received the pressure data detects the pulse wave amplitude from the data on the minute variation in air pressure contained in the pressure data. When the pressure application to the arm in the first stage is continued at the same pressure, basically, or ideally, the pulse wave amplitude remains the same. The same holds true when the pressure application in the second stage, the pressure application in the third stage, are executed. The pulse wave measuring module 12F detects the pulse wave amplitude at a time at which the pressure application in the first stage is performed, and also detects the pulse wave amplitudes at times at which the pressure application in the second stage, the pressure application in the third stage, are performed. As described above, the pulse wave amplitude increases as the tightening pressure applied to the arm by the pressure applying belt 2, which gradually increases every time the stage is raised, becomes closer to the internal pressure applied to the vascular wall, and the pulse wave amplitude decreases after the tightening pressure exceeds the internal pressure applied to the vascular wall. When, in a certain stage, the pulse wave amplitude becomes smaller than that in the previous stage, the pulse wave measuring module 12F generates data specifying the pressure of the air inside the gas bladder 2X at that time point (data corresponding to the air pressure inside the gas bladder 2X at the time at which the pressure application in the fourth stage is performed in FIG. 6(A)), and transmits the generated data to the control module 12C.

As is apparent from the above description, assuming that the pressure specified by this data is set as the pressure of the air inside the gas bladder 2X, the pressure applied to the arm by the pressure applying belt 2 always exceeds the pressure at which the pulse wave amplitude in the artery of the subject becomes maximum (no tension is applied to the vascular wall of the artery).

When the control module 12C receives the data specifying the pressure of the air inside the gas bladder 2X in the stage in which the pulse wave amplitude has become smaller than that in the previous stage from the pulse wave measuring module 12F, the control module 12C generates data indicating that the start pressure determination processing is to be ended, and transmits the data to the pressure control module 12D. When the pressure control module 12D receives the data, the pressure control module 12D ends the start pressure determination processing. That is, the pressure application in the subsequent stage is not to be performed. That is, the "required number of times" of pressure application is ended.

In this embodiment, after the start pressure determination processing is ended, the control module 12C automatically and successively starts the latter stage of the pre-processing. The latter stage of the pre-processing is processing for identifying the pulse wave amplitude in the state in which no tension is applied to the vascular wall when the subject is in a resting state.

When the latter stage of the pre-processing is to be executed, the control module 12C transmits information indicating that the latter stage of the pre-processing is to be executed to the pressure control module 12D, the maximum pulse wave pressure identifying module 12E, and the pulse wave measuring module 12F. The control module 12C also generates three pieces of pressure control data to be used when the latter stage of the pre-processing, the treatment processing, and the post-processing are executed, and transmits those pieces of pressure control data to the auxiliary recording unit 18 through the output module 12B. Then, the control module 12C again reads out the pressure control data to be used in the latter stage of the pre-processing from the auxiliary recording unit 18, and transmits the pressure control data to the pressure control module 12D. The pressure control data at this time is such data as described later.

In the timing chart of FIG. 6(A), the part denoted by reference symbol "B" represents a time slot in which the latter stage of the pre-processing is being executed.

In the latter stage of the pre-processing in this embodiment, as illustrated in FIG. 6(A), for example, the pressure of the air inside the gas bladder 2X of the pressure applying belt 2 is sharply increased in about 3 seconds to about 5 seconds, and is then smoothly and gradually decreased. The entirety, namely, time slots denoted by reference symbols "S" and "B" in FIG. 6(A), of the pre-processing including the time slot in which the pressure of the air inside the gas bladder 2X is smoothly decreased is a state in which the first phase referred to in the present application is being executed. Changing the pressure of the air of the gas bladder 2X over time in this manner (once steeply increasing the pressure and then gradually decreasing the pressure) is the content of the pressure control data in the latter stage of the pre-processing, which has been generated by the control module 12C and transmitted to the pressure control module 12D. A time period required for smoothly decreasing the pressure of the air inside the gas bladder 2X is, for example, about 30 seconds to about 60 seconds, but may be about 90 seconds. However, the time period required for smoothly decreasing the pressure of the air inside the gas bladder 2X varies depending on, for example, a capacity of the gas bladder 2X, and hence the length of the time period has no important meaning.

The pressure of the air inside the gas bladder 2X at the first time point of the latter stage of the pre-processing (first time point from which the pressure of the air inside the gas bladder 2X is smoothly decreased) is equal to the pressure obtained when the final stage (fourth stage in this embodiment) was executed at the time of the start pressure determination processing. As described in the above, start pressure determination processing, the data specifying the pressure of the air inside the gas bladder 2X in the stage in which the pulse wave amplitude has become smaller than that in the previous stage is transmitted from the pulse wave measuring module 12F to the control module 12C, and hence the control module 12C generates pressure control data so that the pressure specified by this data becomes the pressure at the first time point of the latter stage of the pre-processing.

Figure 7:
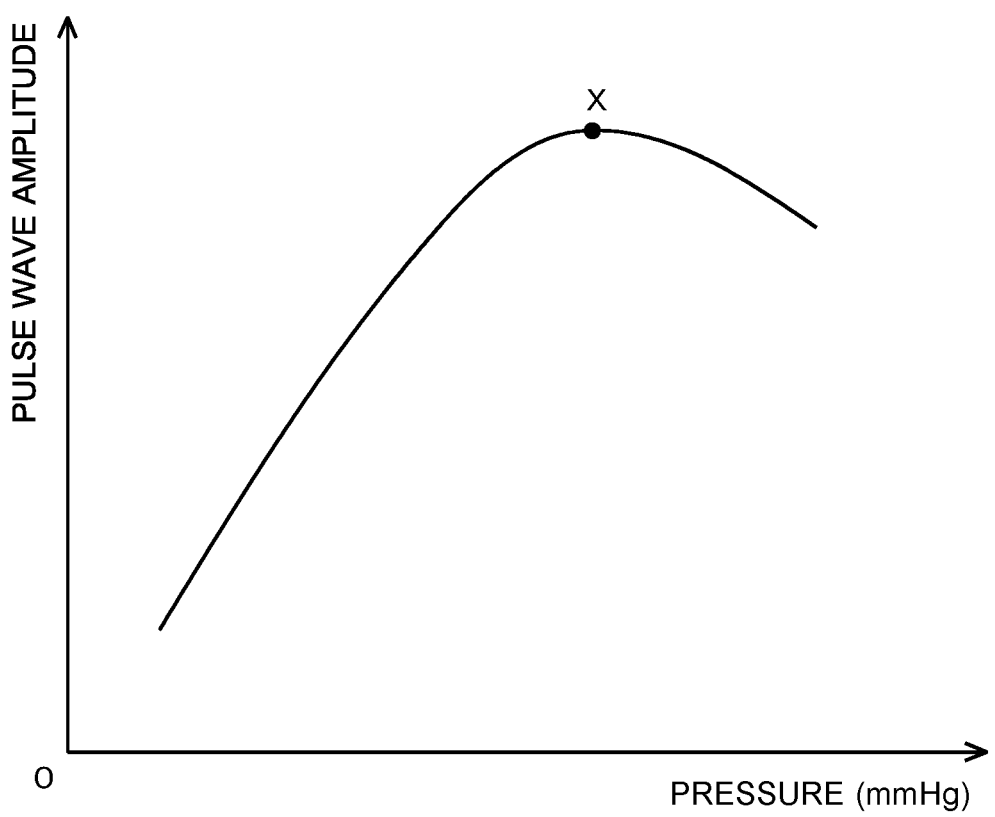
FIG. 7 is a graph for showing a relationship between a pulse wave amplitude and a pressure of air inside the gas bladder at the time at which the pre-processing is executed in the blood vessel training system illustrated in FIG. 1.

In the latter stage of the pre-processing, the pressure of the air inside the gas bladder 2X is smoothly and gradually decreased from the pressure at the first time point. The pressure of the air inside the gas bladder 2X is decreased until the tightening force applied to the arm by the pressure applying belt 2 falls below the pressure at which the pulse wave amplitude in the artery of the subject becomes maximum (no tension is applied to the vascular wall of the artery). That is, the changing of the pressure performed in the latter stage of the pre-processing passes the pressure at which the pulse wave amplitude becomes maximum. As described above, the pressure of the air inside the gas bladder 2X at the first time point of the latter stage of the pre-processing is set so that the pressure applied to the arm by the pressure applying belt 2 certainly exceeds the pressure at which the pulse wave amplitude in the artery of the subject becomes maximum (no tension is applied to the vascular wall of the artery). Therefore, when the pressure of the air inside the gas bladder 2X is decreased so as to certainly fall below the pressure at which the pulse wave amplitude becomes maximum (no tension is applied to the vascular wall of the artery), the pressure applied to the arm by the pressure applying belt 2, which changes in the pre-processing, always passes the pressure at which the pulse wave amplitude becomes maximum. The smallest pressure of the gas inside the gas bladder 2X in the pre-processing can be set to, for example, the normal pressure or the pressure in the first stage being the first part of the start pressure determination processing. In this embodiment, the latter pressure is basically adopted, and in order to give some margin, the pressure of the air inside the gas bladder 2X is decreased to a pressure slightly smaller than the latter pressure, as is the case in this embodiment. In order to similarly give some margin toward a larger pressure, the pressure of the air inside the gas bladder 2X at the first time point of the latter stage of the pre-processing, that is, the first time point from which the pressure is smoothly decreased may be set slightly larger by, for example, about 10 mmHg than the pressure applied to the air inside the gas bladder 2X in the final stage of the start pressure determination processing. While the latter stage of the pre-processing is being executed, in more detail, during at least the time slot in which the pressure of the air inside the gas bladder 2X is smoothly decreased, the pressure data is constantly repeatedly input to the pulse wave measuring module 12F. Therefore, the pulse wave measuring module 12F is in the state of constantly monitoring the pulse wave amplitude at that time point. As described above, while pulse waves are caused in the artery by a heartbeat, the pulse wave amplitude becomes maximum when no tension is applied to the vascular wall, and decreases irrespective of whether the internal pressure is larger or smaller than that. As the pressure of the air inside the gas bladder 2X is decreased, as shown in FIG. 7, the pulse wave amplitude draws an upwardly convex parabolic graph in which the pulse wave amplitude increases until the pressure of the air inside the gas bladder 2X reaches a certain value, and then decreases. In the latter stage of the pre-processing, this graph is drawn from the right side to the left side.

The pulse wave measuring module 12F generates pulse wave data being data specifying the pulse wave amplitude at the time point (time point of X of FIG. 7) at which the pulse wave amplitude became maximum. The pulse wave data is transmitted from the pulse wave measuring module 12F to the recording unit 12G. This pulse wave data is the pre-maximum pulse wave amplitude data specifying the pre-maximum pulse wave amplitude being the maximum pulse wave amplitude exhibited in the latter stage of the pre-processing. The pre-maximum pulse wave amplitude data transmitted to the recording unit 12G is recorded in the recording unit 12G.

Meanwhile, the pulse wave measuring module 12F transmits the data specifying the timing at which the pulse wave amplitude became maximum to the maximum pulse wave pressure identifying module 12E. The maximum pulse wave pressure identifying module 12E that has received the data generates maximum pulse wave pressure data being the data specifying the maximum pulse wave pressure corresponding to the pressure of the air inside the gas bladder 2X at the time point at which the pulse wave amplitude became maximum in the latter stage of the pre-processing. The generated maximum pulse wave pressure data is transmitted from the maximum pulse wave pressure identifying module 12E to the recording unit 12G. The recording unit 12G records the maximum pulse wave pressure data.

In all, the recording unit 12G records the pre-maximum pulse wave amplitude data and the maximum pulse wave pressure data.

After the above-mentioned process, the latter stage of the pre-processing is ended. Accordingly, the pre-processing is ended.

In this embodiment, when the latter stage of the pre-processing is executed, the pressure of the air inside the gas bladder 2X is changed in a direction of decreasing the air pressure, but may be changed in a direction of increasing the air pressure (FIG. 6(B)). However, in an actual case, in comparison between the processing for injecting air into the gas bladder 2X and the processing for exhausting air from the gas bladder 2X, the latter processing can more easily cause the pressure to be smoothly changed. Therefore, when the latter processing is adopted, it is easier to identify more accurate maximum pulse wave pressure data at the time of the pre-processing.

Figure 8:
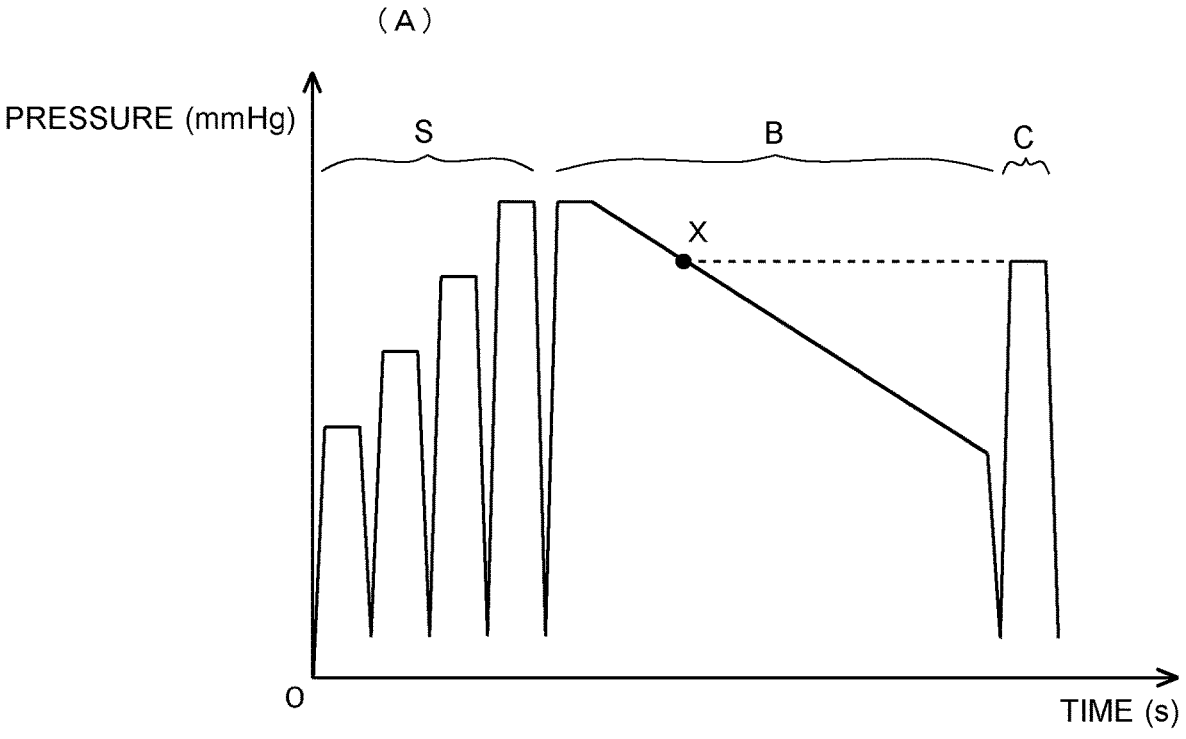
FIG. 8 are graphs for showing a relationship between the pulse wave amplitude and the pressure of air inside the gas bladder at the time at which the pre-processing is executed in another example of the blood vessel training system illustrated in FIG. 1.
Figure 8:
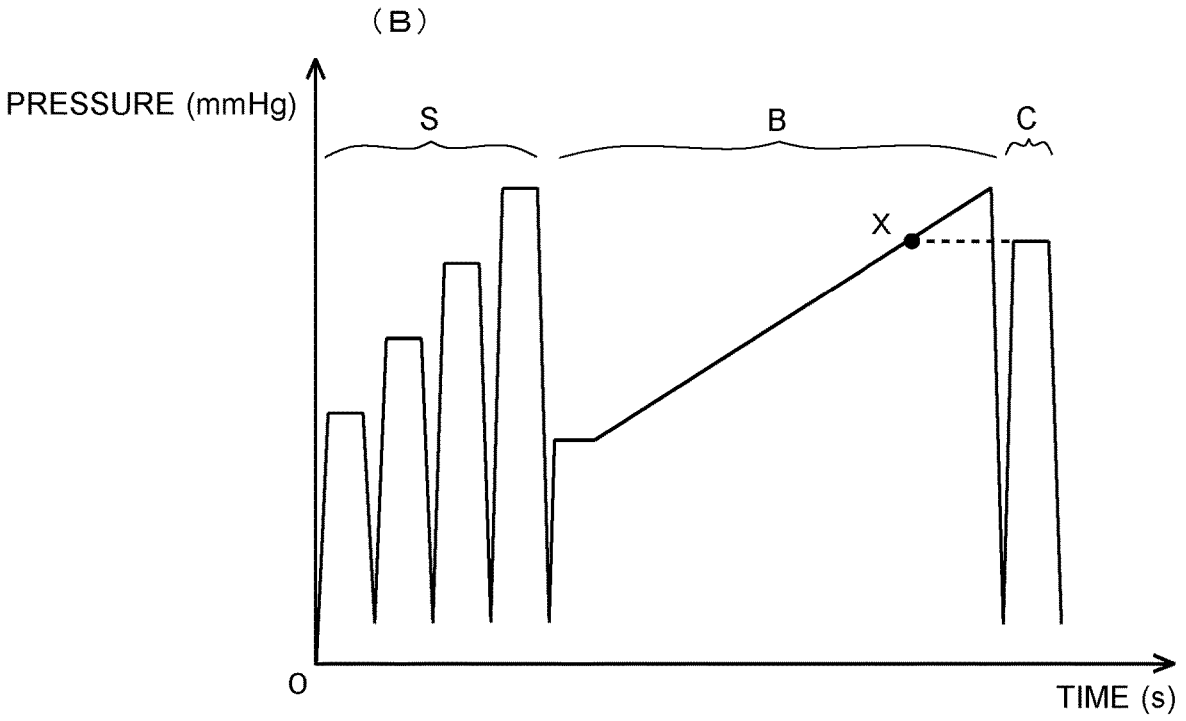

The pre-processing can be set as illustrated in FIG. 8. In this case, a method of determining the pre-maximum pulse wave amplitude differs from that in the above-mentioned case.

In processing executed in the pre-processing in this case, the former stage S and the latter stage B, which are described above, are the same as those in the above-mentioned example. In the latter stage B, the pre-maximum pulse wave amplitude and the maximum pulse wave pressure are obtained through the same kinds of processing as those in the above-mentioned example. However, in examples using the timing charts illustrated in FIGS. 8, the pre-maximum pulse wave amplitude obtained in the latter stage B is merely a temporary pre-maximum pulse wave amplitude (tentative pre-maximum pulse wave amplitude), and a true pre-maximum pulse wave amplitude is obtained while processing denoted by reference symbols "C" (hereinafter referred to as "constant pressure processing"), which further follows the latter stage B, is being executed. The constant pressure processing C may succeed the timing chart of FIG. 6(A) (FIG. 8(A)), or may succeed the timing chart of FIG. 6(B) (FIG. 8(B)).

In the latter stage B of each of FIGS. 8, the timing denoted by reference symbol "X" is a timing at which the tentative pre-maximum pulse wave amplitude was observed. The pressure of the air inside the gas bladder 2X at that time is the maximum pulse wave pressure.

The constant pressure processing C illustrated in each of FIG. 8 is processing for keeping the pressure of the air inside the gas bladder 2X at the maximum pulse wave pressure obtained in the latter stage B. A time period in which the pressure of the air inside the gas bladder 2X is kept at the maximum pulse wave pressure is, for example, about 5 seconds to about 15 seconds, preferably about 10 seconds. Such pressure control data required for executing the constant pressure processing C is generated by the control module 12C, and irrespective of whether or not to be temporarily recorded in the auxiliary recording unit 18, the pressure control data is supplied from the control module 12C to the pressure control module 12D.

In the examples illustrated in FIGS. 8, throughout a period in which the constant pressure processing C is being performed, the pulse wave amplitude is monitored by the pulse wave measuring module 12F based on the pulse wave data transmitted from the control module 12C. In this case, while the constant pressure processing C is being performed, the tightening force applied to the arm by the pressure applying belt 2 is constant, and hence the tension applied to the vascular wall remains constant. Therefore, as long as the subject maintains the resting state, the measured pulse wave amplitude is basically supposed to be constant. However, a peak of the pulse wave occurs only at a timing of the heartbeat, that is, only once per approximately one second in most cases, and hence the pulse wave amplitude obtained when a timing at which the peak of the pulse wave occurs while the constant pressure processing C is being performed exactly matches a timing of sampling performed by the pulse wave measuring module 12F several times to several tens of times per second is exhibited to a larger extent than the pulse wave amplitude obtained otherwise. In the constant pressure processing C, under a state in which the pressure of the air inside the gas bladder 2X is kept at the maximum pulse wave pressure, when the pulse wave amplitude is sampled, for example, about 10 times in 10 seconds, the largest pulse wave amplitude thereamong is extremely likely to be the correct value as the pre-maximum pulse wave amplitude of the subject obtained when the subject is in a resting state and in the state in which no tension is applied to the vascular wall.

Meanwhile, the above-mentioned tentative pre-maximum pulse wave amplitude is determined by sampling at only one timing at which the maximum pulse wave pressure occurred, and therefore may lack some accuracy in some cases. Through execution of the constant pressure processing C, such a problem can be eliminated.

Next, the treatment processing is executed.

In this embodiment, after the pre-processing is ended, the control module 12C automatically and successively starts the treatment processing. The treatment processing is processing for carrying out a blood flow restriction training method. When the treatment processing is carried out, the subject may maintain the resting state, or may perform a hand open-and-close exercise or another light exercise.

When the treatment processing is to be executed, the control module 12C transmits information indicating that the treatment processing is to be executed to the pressure control module 12D. The control module 12C also reads out, from the auxiliary recording unit 18, the previously generated pressure control data to be used when the treatment processing is executed, and transmits the pressure control data to the pressure control module 12D. The pressure control data at this time is such data as described later.

When the pressure control data to be used in the treatment processing is generated by the control module 12C, the control module 12C reads out the maximum pulse wave pressure data recorded in the recording unit 12G, and executes a predetermined calculation operation on the maximum pulse wave pressure specified by the maximum pulse wave pressure data to obtain a treatment pressure, which is a pressure smaller than the maximum pulse wave pressure. The treatment pressure is a pressure serving as an upper limit of the pressure of the air inside the gas bladder 2X, which is used when the treatment processing is being executed. The treatment pressure can be set to, for example, a pressure obtained by subtracting a certain pressure (e.g., 10 mmHg to 50 mmHg) from the maximum pulse wave pressure or a pressure obtained by multiplying the maximum pulse wave pressure by a value of 0.6 to 0.9.

In the treatment processing, a second phase is executed. The second phase is processing for keeping the pressure of the air inside the gas bladder 2X during a predetermined time period between 1 minute and 15 minutes at such a ratio that the time period in which the pressure of the air inside the gas bladder 2X is equal to or smaller than the treatment pressure and equal to or larger than 30 mmHg is 50% or larger and the time period in which the pressure of the air inside the gas bladder 2X is smaller than 30 mmHg is 50% or smaller, and then decreasing the pressure of air inside the gas bladder to smaller than 30 mmHg.

Figure 9:
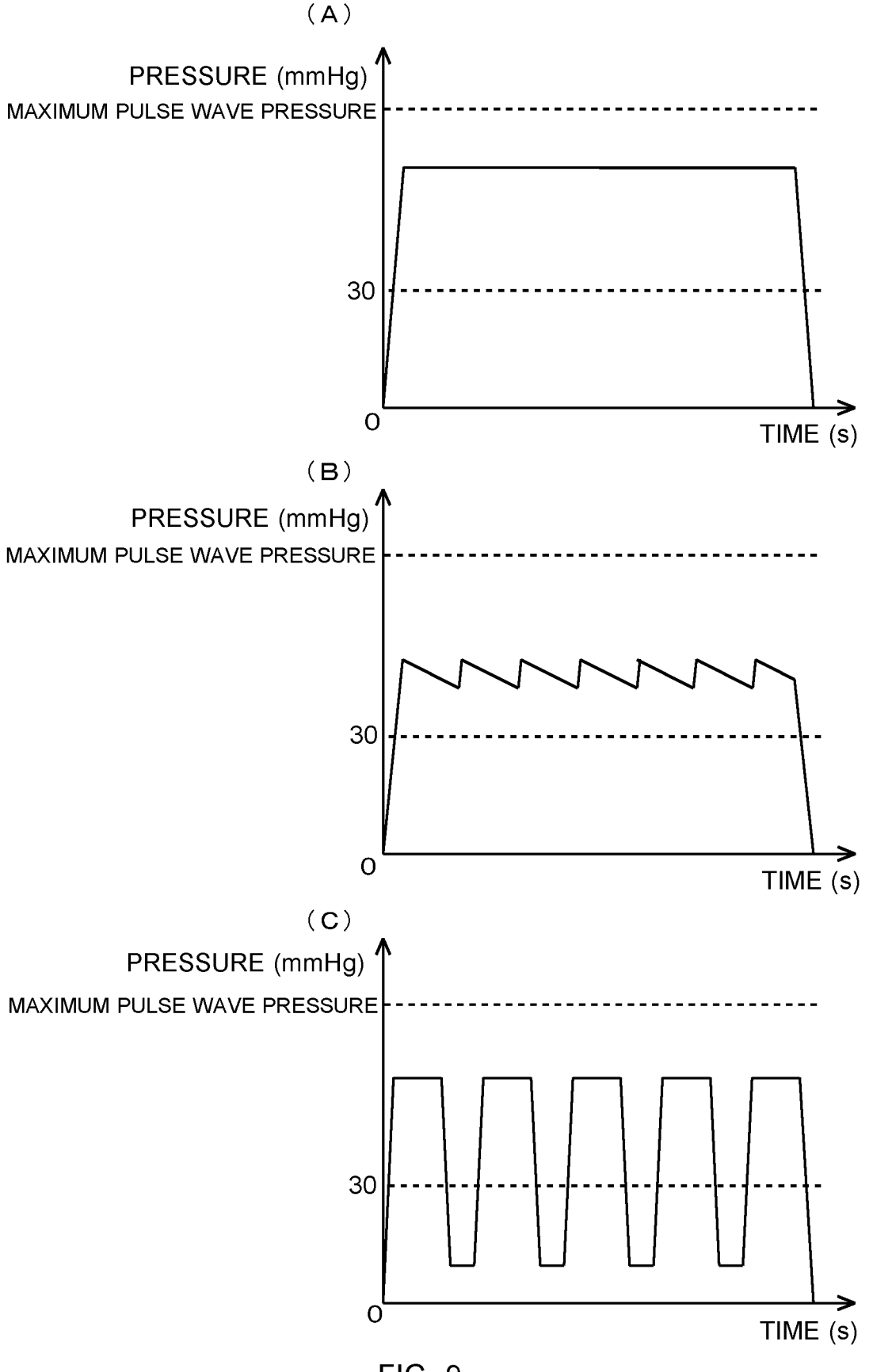
FIG. 9 are timing charts for illustrating the pressure of air inside the gas bladder at a time at which treatment processing is executed in the blood vessel training system illustrated in FIG. 1.

The pressure of air inside the gas bladder 2 in the second phase is illustrated in FIG. 9(A), FIG. 9(B), and FIG. 9(C). The representation method of FIG. 9 is similar to that of FIG. 6.

In the example of FIG. 9(A), the pressure of the air inside the gas bladder 2X of the pressure applying belt 2 is sharply increased in, for example, about 3 seconds to about 5 seconds, and then the pressure is kept for at least 1 minute or at most 15 minutes, preferably 5 minutes to 10 minutes, in this embodiment, for example, 5 minutes, to which the present embodiments are not limited. After that, the pressure is decreased to, for example, the normal pressure in about several seconds. The pressure of the air inside the gas bladder 2X during a period in which the pressure is kept constant is, in this embodiment, a pressure obtained by multiplying the maximum pulse wave pressure by a value of 0.8. This pressure is the treatment pressure, and in the example of FIG. 9(A), the pressure of the air inside the gas bladder 2X is kept at the treatment pressure except for the first part and the last part of the treatment processing. In this example, the start time point of a time slot in which the pressure is kept constant is the start of the second phase, and the end time point of the time slot in which the pressure is kept constant is the end of the second phase. In this example, throughout a period in which the second phase is being executed, the pressure of the air inside the gas bladder 2X is constant, and a time slot in which the pressure of the air inside the gas bladder 2X is equal to or smaller than the treatment pressure and equal to or larger than 30 mmHg occupies 100% of the time slot in which the second phase is being executed.

In the example of FIG. 9(B), the pressure of the air inside the gas bladder 2X of the pressure applying belt 2 is sharply increased in, for example, about 3 seconds to about 5 seconds. After that, during the same time slot as that in the example of FIG. 9(A), with the treatment pressure being set as an upper-side peak and a pressure larger than 30 mmHg and smaller than the upper-side peak being set as a lower-side peak, the pressure rises and falls between the upper-side peak and the lower-side peak. In this example, the first upper-side peak is the start of the second phase, and the last lower-side peak is the end of the second phase. In this example, the pressure of the air inside the gas bladder 2X varies while the second phase is being executed, but in this example as well, the time slot in which the pressure of the air inside the gas bladder 2X is equal to or smaller than the treatment pressure and equal to or larger than 30 mmHg occupies 100% of the time slot in which the second phase is being executed. In this example, restriction and release of blood flow of the artery alternately occurs, thereby increasing an effect of achieving the elasticity of the blood vessel.

In the example of FIG. 9(C), the pressure of the air inside the gas bladder 2X of the pressure applying belt 2 is sharply increased in, for example, about 3 seconds to about 5 seconds. After that, during the same time slot as that in the example of FIG. 9(A), after having been kept at the treatment pressure for a predetermined time period, the pressure of the air inside the gas bladder 2X is sharply decreased in 3 seconds to 5 seconds, and a pressure smaller than 30 mmHg is kept for a predetermined time period. Assuming that a time slot in which an upper-side constant pressure larger than 30 mmHg is kept is referred to as a first time slot and a time slot in which a lower-side constant pressure smaller than 30 mmHg is kept is referred to as a second time slot, the first time slot and the second time slot are each repeated a plurality of times after that. A duration of the first time slot per time is set to a predetermined length between 15 seconds to 35 seconds. Further, a duration of the second time slot per time is set to a predetermined length between 15 seconds to 35 seconds. The number of times the first time slot and the second time slot are alternately repeated is determined based on a length of each of the first time slot and the second time slot and a length from the start point to the end point for executing the second phase. In this example, a time point at which the first-position first time slot is started is the start of the second phase, and a time point at which the last-position first time slot is ended is the end of the second phase. The constant pressure in each first time slot is set the same in this embodiment, but the present embodiments are not limited thereto. Further, the constant pressure in each second time slot is set the same in this embodiment, but the present embodiments are not limited thereto. Further, the length of each first time slot is set the same in this embodiment, but the present embodiments are not limited thereto. Further, the length of each second time slot is set the same in this embodiment, but the present embodiments are not limited thereto. Further, in this embodiment, the length of the first time slot is shorter than the length of the second time slot, but the present embodiments are not limited thereto. For example, all the first time slots and all the second time slots may be set to have the same length.

When the second phase is ended, the air pressure inside the gas bladder 2X is decreased to a pressure smaller than 30 mmHg in 3 seconds to 5 seconds after the last-position first time slot is ended. In this example, the pressure of the air inside the gas bladder 2X varies while the second phase is being executed, and in the first time slot, the pressure of the air inside the gas bladder 2X is equal to or smaller than the treatment pressure and equal to or larger than 30 mmHg, while in the second time slot, the pressure of the air inside the gas bladder 2X is smaller than 30 mmHg. Then, in this example, in the second phase, a ratio occupied by a total time length of all the first time slots is set equal to or larger than 50%, and a ratio occupied by a total time length of all the second time slots is set equal to or smaller than 50%. In this example as well, the restriction and the release of the blood flow of the artery alternately occurs, thereby increasing the effect of achieving the elasticity of the blood vessel.

In any one of the examples illustrated in FIG. 9(A) to FIG. 9(C), the tightening force is applied to the limb of the subject from the gas bladder 2X through the treatment processing, and the blood flow restriction training is thereby executed.

The time period for subjecting the limb to the tightening is set to 1 minute or longer for a reason that at least 1 minute is required to cause a change in the elasticity of the blood vessel before and after the pressure application based on release of nitric oxide. The time period is set to 15 minutes or shorter for the purpose of suppressing a burden on a body of the subject. According to the experiments performed by the inventor of the present application, it has been found that the above-mentioned time period set to about 5 minutes is sufficient for achieving the elasticity of the blood vessel based on the release of nitric oxide.

A level to which the air pressure inside the gas bladder 2X is to be decreased when the tightening of the limb is released may be appropriately determined within a range that allows the elasticity of the blood vessel to change due to the released blood flow and a range smaller than 30 mmHg. In this embodiment, the pressure of the air inside the gas bladder 2X is set to be decreased to the normal pressure, but an air pressure of about 20 mmHg may remain in the gas bladder 2X even in a stage in which the tightening of the limb is released, as is somewhat meaningless.

In the treatment processing, the pulse wave amplitude is not required to be measured.

In this embodiment, the pressure of the air inside the gas bladder 2X is returned to the normal pressure, and the treatment processing is ended.

When the treatment processing is executed, the subject may perform light training with the limb being tightened. Examples of the light training include the hand open-and-close exercise. This can cause a further increase in nitric oxide in the blood and cause a greater change in elasticity of the blood vessel at the time point at which each of the pre-processing and the post-processing is being executed. In this case, the pressure applying belt 2 remains in a state of being connected to the blood vessel training device 1. When the subject performs exercise under such a state, the muscle of the arm becomes wider to increase the pressure of the air inside the gas bladder 2X, thereby causing a fear of falling out of the pressure illustrated in each of the timing charts of FIG. 9(A), FIG. 9(B), and FIG. 9(C). In such a case, the pressure control module 12D generates second control data to cause the proportional valve 15 to be driven, thereby being capable of keeping the pressure inside the gas bladder 2X constant. More specifically, the pressure control module 12D that has generated second control data in accordance with an instruction from the control module 12C transmits the second control data to the proportional valve 15 through the output module 12B. The proportional valve 15 receives the second control data, and executes the above-mentioned processing based on the second control data. When such processing is not required, the proportional valve 15 is not required. When the subject performs light exercise without presence of the proportional valve 15, even in a case in which the pressure control data used in the treatment processing indicates that the pressure of the gas inside the gas bladder 2X is to be kept at such a constant pressure as illustrated in the example of FIG. 9(A), the tightening force applied to the limb by the pressure applying belt 2 rises and falls. Further, in the example illustrated in FIG. 9(C) as well, variation occurs in the pressure of the air inside the gas bladder 2X in each of the first time slot and the second time slot, which is originally supposed to be constant. However, such variation of the pressure of the air inside the gas bladder 2X that falls out of a scheduled tightening force is permitted. This is because, when there is such variation of the tightening force, an increase in elasticity of the blood vessel can even be expected than scheduled, for the same reason as that described with reference to FIG. 9(B), that is, through repetitions of the restriction and the release of the blood flow.

In this embodiment, after the treatment processing is ended, the control module 12C automatically starts the post-processing. In the post-processing, the post-maximum pulse wave amplitude is measured.

When the post-processing is to be executed, the control module 12C transmits information indicating that the post-processing is to be executed to the pressure control module 12D. The control module 12C also reads out, from the auxiliary recording unit 18, the previously generated pressure control data to be used when the post-processing is executed, and transmits the pressure control data to the pressure control module 12D. The pressure control data at this time is such data as described later.

When the post-processing is carried out, the third phase is executed. The third phase is processing for changing the pressure of the gas inside the gas bladder 2X within at least a range of +10 mmHg of the maximum pulse wave pressure so as to pass the maximum pulse wave pressure, or keeping the pressure of the gas inside the gas bladder 2X within a range equal to or larger than the maximum pulse wave pressure and equal to or smaller than a pressure larger by 20 mmHg than the maximum pulse wave pressure, during a time slot between a start point, which is a predetermined timing at which 45 seconds have not elapsed from the end of the treatment processing, and an end point, which is a predetermined timing at which at least 100 seconds have elapsed from the end of the treatment processing.

That is, in the third phase, the pressure of the air inside the gas bladder 2X in the time slot from the start point to the end point is controlled in one of two manners described below.

The first one is processing for changing the pressure of the gas inside the gas bladder 2X within at least the range of ±10 mmHg of the maximum pulse wave pressure so as to pass the maximum pulse wave pressure. The second one is processing for keeping the pressure of the gas inside the gas bladder 2X within the range equal to or larger than the maximum pulse wave pressure and equal to or smaller than the pressure larger by 20 mmHg than the maximum pulse wave pressure.

The start point can be appropriately selected from a time slot in which 45 seconds have not elapsed from the end of the treatment processing. The end point can be appropriately selected from a time slot in which 100 seconds have elapsed from the end of the treatment processing. That is, in a time slot in which 45 seconds have elapsed from the end of the treatment processing and before 100 seconds have elapsed, the pressure of the air inside the gas bladder 2X is always kept in a state described above in one of the two patterns of processing described above, and the pulse wave amplitude is measured during that time slot. This is because the post-maximum pulse wave amplitude often occurs during a period between a time point at which 45 seconds have elapsed from the end of the treatment processing and a time point at which 100 seconds have elapsed from the end of the treatment processing. In order to give some margin, for example, the start point may be set to a predetermined timing at which 40 seconds have not elapsed since 5 seconds elapsed from the end of the treatment processing. Meanwhile, the end point may be set at a predetermined timing at which 200 seconds have not elapsed since 120 seconds elapsed from the end of the treatment processing. When the start point and the end point are set within such a range, a correct post-maximum pulse wave amplitude can be measured with reliability.

When the pressure control data to be used in the post-processing is generated in advance by the control module 12C, the maximum pulse wave pressure is required. Therefore, the control module 12C reads out the maximum pulse wave pressure data recorded in the recording unit 12G, and generates pressure control data in the third phase. When the pressure control data in the third phase is to be generated, for example, data input by the practitioner through operation of the operating unit 16 at a predetermined timing before the pre-processing is started may be used as well.

When the post-processing is to be executed, the control module 12C transmits the information indicating that the post-processing is to be executed to the pressure control module 12D and the pulse wave measuring module 12F. The control module 12C also generates pressure control data to be used when the post-processing is executed, and transmits the pressure control data to the pressure control module 12D. The pressure control data at this time is such data as described later.

Figure 10:
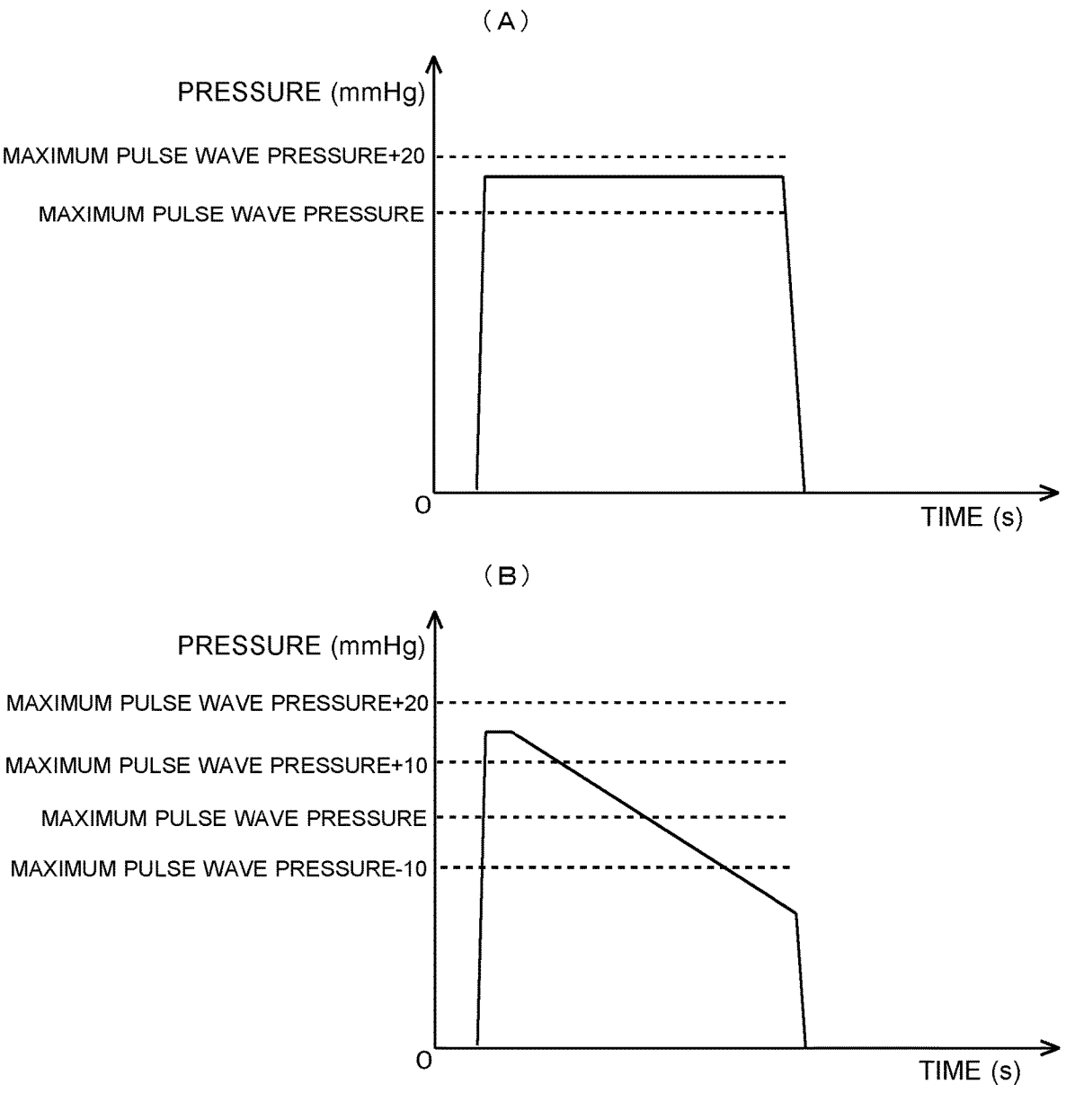
FIG. 10 are timing charts for illustrating the pressure of air inside the gas bladder at a time at which post-processing is executed in the blood vessel training system illustrated in FIG. 1.

In FIGS. 10, an example of a timing chart of the time slot of the post-processing is illustrated. The horizontal axis and the vertical axis are the same as those of FIG. 6.

In the post-processing, as illustrated in FIG. 10(A), during a period from the start point to the end point of the post-processing, the pressure of the air inside the gas bladder 2X of the pressure applying belt 2 may be kept constant within the range equal to or larger than the maximum pulse wave pressure recorded in the recording unit 12G and equal to or smaller than the pressure larger by 20 mmHg than the maximum pulse wave pressure. This is the second example of the above-mentioned two kinds of processing for the third phase. The time point corresponding to the left end of the horizontal part in the timing chart of FIG. 10(A) is the start point, and the time point corresponding to the right end is the end point.

As illustrated in FIG. 10(A), when the pressure of the air inside the gas bladder 2X is kept constant at the range equal to or larger than the maximum pulse wave pressure and equal to or smaller than the pressure larger by 20 mmHg than the maximum pulse wave pressure, the pressure of the air inside the gas bladder 2X at that time may not be the pressure at which the tension applied to the vascular wall is zero, but keeps a state of differing by only 20 mmHg at maximum from the pressure at which the tension applied to the vascular wall is zero. This is because, in the treatment processing, the blood flow restriction training is executed, to thereby cause an increase in the blood pressure in the same manner as when exercise is actually performed, and it is expected to require a corresponding increase in pressure of the air inside the gas bladder 2X for creating a state in which no tension is applied to the vascular wall, but the blood pressure mostly increases by approximately 10 mmHg or about 20 mmHg at maximum. Therefore, in short, the pressure of the air inside the gas bladder 2X at which the maximum pulse wave amplitude is exhibited in the post-processing is present between the maximum pulse wave pressure and the pressure larger than the maximum pulse wave pressure by 20 mmHg, and hence when the pressure of the air inside the gas bladder 2X is kept constant at the range equal to or larger than the maximum pulse wave pressure and equal to or smaller than the pressure larger by 20 mmHg than the maximum pulse wave pressure, the pressure of the air inside the gas bladder 2X keeps the state of differing by only 20 mmHg at maximum from the pressure at which the tension applied to the vascular wall is zero.

Thus, even when the tension applied to the vascular wall is not zero, a state in which the tension applied to the vascular wall is small is kept during the time slot from the start point to the end point. When the tension applied to the vascular wall is small, the pulse wave amplitude is exhibited to a larger extent, and hence such a change in pressure of the gas inside the gas bladder 2X is effective for identifying the post-maximum pulse wave amplitude, which serves as a target to be compared to the pre-maximum pulse wave amplitude. In the example illustrated in FIG. 10(A), the air pressure inside the gas bladder 2X is kept constant in the time slot between the start point and the end point, but the present embodiments are not limited thereto. For example, in this case, the air pressure in the gas bladder 2X may be varied between the maximum pulse wave pressure and the pressure larger by 20 mmHg than that, from which, however, no particular benefit arises.

Further, the pressure of the air inside the gas bladder 2X of the pressure applying belt 2 in the post-processing may be obtained by processing for changing, as illustrated in FIG. 10(B), the pressure of the gas inside the gas bladder 2X within at least the range of ±10 mmHg of the maximum pulse wave pressure so as to pass the maximum pulse wave pressure, with the maximum pulse wave pressure recorded in the recording unit 12G being used as a reference, during a period from the start point to the end point. In the example illustrated in FIG. 10(B), in more detail, the above-mentioned pressure is linearly decreased from a pressure larger than the maximum pulse wave pressure by 10 mmHg or larger and equal to or smaller than a pressure larger by 20 mmHg to a pressure equal to or smaller than the maximum pulse wave pressure by 20 mmHg. This is an example of the above-mentioned first kind of processing for the third phase. The time point corresponding to the left end of the part gently declining rightward over a long time period in the timing chart of FIG. 10(B) is the start point, and the time point corresponding to the right end is the end point.

As described above, the pressure inside the gas bladder at which the post-maximum pulse wave amplitude occurs is mostly larger than the maximum pulse wave pressure by about 10 mmHg or about 20 mmHg at maximum in accordance with the increase in blood pressure of the subject through the treatment processing, and hence when the pressure of the gas inside the gas bladder at the start point is set as described above and the pressure of the gas inside the gas bladder is decreased from that point to a predetermined pressure that is smaller than the maximum pulse wave pressure by 10 mmHg or larger, the post-maximum pulse wave amplitude can be grasped with a significant probability. When the air pressure at the start point is set higher than the maximum pulse wave pressure by 20 mmHg, the post-maximum pulse wave amplitude can be grasped with reliability.

While time elapses from the start point to the end point, the pressure of the gas inside the gas bladder 2X is linearly decreased between the above-mentioned two pressures. In this case, while the pressure of the gas inside the gas bladder 2X is linearly decreased, the force applied to the vascular wall is first directed inward, becomes zero after a while, and is directed outward after that. Again, when the force applied to the vascular wall is zero, no tension is applied to the vascular wall. In the third phase during the post-processing, when the pressure of the gas inside the gas bladder 2X is linearly decreased as described above, the tension applied to the vascular wall is zero for a moment (or a short time period), but in time slots before and after that moment, the tension applied to the vascular wall is small to some extent. The largest pulse wave amplitude among the pulse wave amplitudes measured when such a third phase is being executed is suitable to be identified as the post-maximum pulse wave amplitude, which serves as the target to be compared to the pre-maximum pulse wave amplitude. A time period required for smoothly decreasing the pressure of the air inside the gas bladder 2X is not so important in the same manner as the time period required for smoothly decreasing the pressure of the air inside the gas bladder 2X in the first phase, but may be set, for example, approximately the same as the time period required for smoothly decreasing the pressure of the air inside the gas bladder 2X in the first phase. While the post-processing is being executed, in more detail, during the time slot from the start point to the end point, the pressure data is constantly repeatedly input to the pulse wave measuring module 12F. Therefore, the pulse wave measuring module 12F is in the state of constantly monitoring the pulse wave amplitude at that time point. The elasticity of the vascular wall changes from moment to moment due to an influence of nitric oxide increasing inside the blood, which is exerted by an influence of the blood flow restriction training based on the treatment processing and by the blood flow promoted by the release of the vein at the end of the treatment processing, and the pulse wave amplitude also changes based on the change in elasticity of the vascular wall.

The pulse wave measuring module 12F generates post-maximum pulse wave amplitude data being data specifying the post-maximum pulse wave amplitude corresponding to the pulse wave amplitude at the time point at which the pulse wave amplitude became maximum. The post-maximum pulse wave amplitude data is transmitted from the pulse wave measuring module 12F to the recording unit 12G, and is recorded in the recording unit 12G.

After the above-mentioned process, the post-processing is ended.

In this embodiment, the evaluation processing is executed subsequently to the post-processing, but the present embodiments are not limited thereto. The evaluation processing is processing for evaluating to what extent the elasticity of the blood vessel of the subject has increased between before and after the treatment processing.

When the post-processing is ended, the control module 12C reads out a pair of the pre-maximum pulse wave amplitude data and the post-maximum pulse wave amplitude data on the subject treated in the evaluation-enabled mode, which are recorded in the recording unit 12G. The control module 12C performs a predetermined calculation operation based on the pre-maximum pulse wave amplitude and the post-maximum pulse wave amplitude that are specified by those two pieces of data, to thereby generate evaluation data for evaluating to what extent the elasticity of the blood vessel of the subject has increased between before and after the treatment processing.

In the evaluation processing, for example, when the pre-maximum pulse wave amplitude recorded in the recording unit 12G in the pre-processing is represented by $P_B$ and the post-maximum pulse wave amplitude recorded in the recording unit 12G in the post-processing is represented by $P_A$, a result obtained by calculating $P_A/P_B$ Or $(P_A-P_B)/P_B$ can be used as an evaluation result. In any case, a larger numerical value indicates that the elasticity of the blood vessel of the subject has increased more before and after the treatment processing.

The control module 12C transmits the generated evaluation data to the output module 12B. When the output module 12B receives the evaluation data, the output module 12B generates image data on an image including, for example, characters for use to display the evaluation data on the display unit 17, and transmits the image data to the display unit 17. The display unit 17 that has received the image data displays the image based on the image data. When the image is viewed, the evaluation result regarding how much the elasticity of the blood vessel of the subject has improved before and after the blood flow restriction training is understood.

The evaluation data may be transmitted from the control module 12C to the auxiliary recording unit 18, and recorded in the auxiliary recording unit 18 for later use together with, for example, data (name, ID, or the like) identifying the subject.

In this embodiment, examples of a plurality of pieces of pressure control data including a plurality of timing charts have been described for the pre-processing, the treatment processing, and the post-processing, but the respective pieces of pressure control data given as the examples for the pre-processing, the treatment processing, and the post-processing may be freely selected and combined for each of the pre-processing, the treatment processing, and the post-processing.

Figure 11:
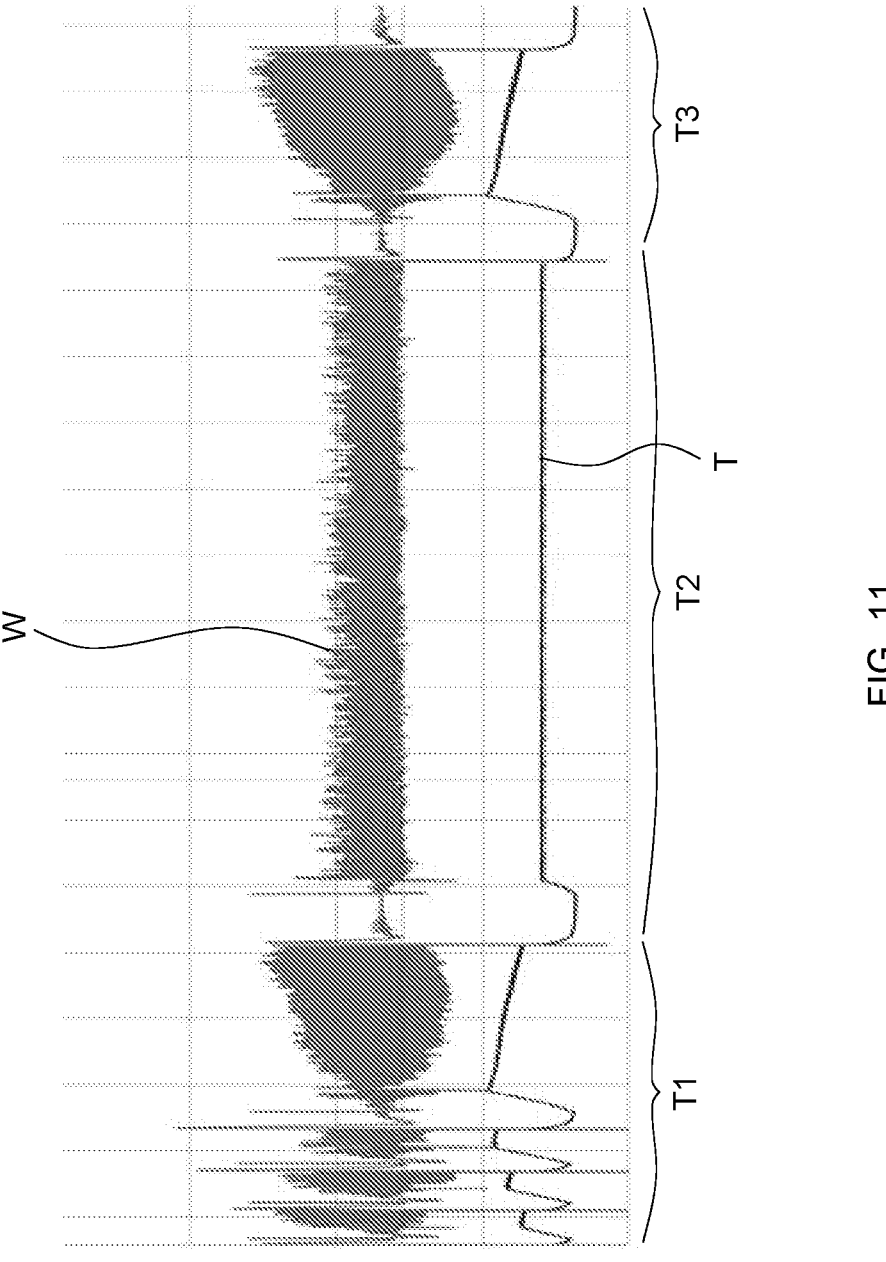
FIG. 11 is a view for illustrating a pulse wave amplitude of a subject exhibited when pre-processing, treatment processing, and post-processing are carried out by a prototype of the blood vessel training system.

Just for reference, FIG. 11 is an illustration of an example of an experiment in which a prototype was used to measure the pulse wave amplitude of the subject.

In FIG. 11, T represents the timing chart of the pressure of the air inside the gas bladder 2X, and W represents the pulse wave amplitude. In the timing chart, T1 represents the pre-processing, T2 represents the treatment processing, and T3 represents the post-processing.

It can be observed that the pulse wave amplitude in the post-processing is larger than the pulse wave amplitude in the pre-processing. It is obvious that the post-maximum pulse wave amplitude is larger than the pre-maximum pulse wave amplitude.

Test conditions therefor were as follows. The timing chart illustrated in FIG. 6(A) was selected for the pre-processing T1, the timing chart illustrated in FIG. 9(A) was selected for the treatment processing T2, and the timing chart illustrated in FIG. 10(B) was selected for the post-processing T3. The wearing pressure was 18 mmHg, the pressure of the air inside the gas bladder 2X in the treatment processing was set constant at 0.6 time the maximum pulse wave pressure, the pressure application time period in which the pressure was set constant at 0.6 times the maximum pulse wave pressure in the treatment processing was 5 minutes, and the subject maintained a stable state in the treatment processing.

The invention claimed is:

1. A blood vessel training device, which is configured to form a blood vessel training system for increasing elasticity of a blood vessel in combination with:

a tightener including:

a belt having a length that allows the belt to be wrapped around a predetermined portion of any one of limbs of a subject;

a fixing member configured to fix the belt under a state in which the belt is wrapped around the predetermined portion of the one of the limbs; and a gas bladder, which is provided to the belt, and is configured to apply a predetermined tightening pressure to the predetermined portion of the one of the limbs by tightening the predetermined portion of the one of the limbs through loading of a gas inside the gas bladder under a state in which the belt wrapped around the predetermined portion of the one of the limbs is fixed by the fixing member;

a pressure varying device configured to set a pressure of the gas inside the gas bladder to a desired pressure; and a pulse wave measuring device configured to measure, in a vicinity of a portion of the one of the limbs at which the tightener is fixed or on a further distal end side of the one of the limbs relative to the portion, a predetermined parameter varying in accordance with a variation of a magnitude of a pulse wave of an artery, and generate pulse wave data on a pulse wave amplitude based on the predetermined parameter, the blood vessel training device comprising:

a control module configured to receive the pulse wave data from the pulse wave measuring device and control the pressure varying device; and a recording unit configured to record data, wherein the control module is configured to execute:

pre-processing for: controlling the pressure varying device so as to cause the pressure varying device to execute a first phase, which is processing including at least changing the pressure of the gas inside the gas bladder so as to pass a range in which the pulse wave amplitude is expected to become maximum; performing at least processing for receiving the pulse wave data a plurality of times from the pulse wave measuring device while the first phase is being executed, to thereby identify a pre-maximum pulse wave amplitude, which is a pulse wave amplitude that became maximum while the first phase was being executed, and a maximum pulse wave pressure, which is the pressure of the gas inside the gas bladder at a time at which the pre-maximum pulse wave amplitude occurred; and recording the pre-maximum pulse wave amplitude and the maximum pulse wave pressure in the recording unit;

treatment processing for controlling the pressure varying device so as to cause the pressure varying device to execute a second phase, which is processing for executing a predetermined calculation operation on the maximum pulse wave pressure recorded in the recording unit to obtain a treatment pressure, which is a pressure smaller than the maximum pulse wave pressure, keeping the pressure of the gas inside the gas bladder during a predetermined time period between 1 minute and 15 minutes at such a ratio that a time period in which the pressure of the gas inside the gas bladder is equal to or smaller than the treatment pressure and equal to or larger than 30 mmHg is 50% or larger and a time period in which the pressure of the gas inside the gas bladder is smaller than 30 mmHg is 50% or smaller, and then decreasing the pressure of the gas inside the gas bladder to 30 mmHg or smaller, the treatment processing being executed subsequently to the pre-processing;

post-processing for: controlling the pressure varying device so as to cause the pressure varying device to execute a third phase, which is processing for changing the pressure of the gas inside the gas bladder within at least a range of +10 mmHg of the maximum pulse wave pressure recorded in the recording unit so as to pass the maximum pulse wave pressure, or keeping the pressure of the gas inside the gas bladder within a range equal to or larger than the maximum pulse wave pressure recorded in the recording unit and equal to or smaller than a pressure larger by 20 mmHg than the maximum pulse wave pressure recorded in the recording unit, during a period between a start point, which is a predetermined timing at which 45 seconds have not elapsed from an end of the treatment processing, and an end point, which is a predetermined timing at which at least 100 seconds have elapsed from the end of the treatment processing; performing processing for receiving the pulse wave data a plurality of times from the pulse wave measuring device while the third phase is being executed, to thereby identify a post-maximum pulse wave amplitude, which is a pulse wave amplitude that became maximum while the third phase was being executed; and recording the post-maximum pulse wave amplitude in the recording unit, the post-processing being executed subsequently to the treatment processing; and evaluation processing for evaluating a state of the blood vessel of the subject through use of the pre-maximum pulse wave amplitude and the post-maximum pulse wave amplitude that are recorded in the recording unit, the evaluation processing being executed after the post-processing.

2. The blood vessel training device according to claim 1, wherein the control module is configured to, in the pre-processing: control the pressure varying device so as to cause the pressure varying device to execute the first phase, which is processing including causing the pressure varying device to execute processing for decreasing the pressure of the gas inside the gas bladder so as to pass the range in which the pulse wave amplitude is expected to become maximum; perform processing for receiving the pulse wave data a plurality of times from the pulse wave measuring device while the pressure varying device is decreasing the pressure of the gas inside the gas bladder, to thereby identify the pre-maximum pulse wave amplitude, which is the pulse wave amplitude that became maximum while the pressure varying device was decreasing the pressure of the gas inside the gas bladder, and the maximum pulse wave pressure, which is the pressure of the gas inside the gas bladder at the time at which the pre-maximum pulse wave amplitude occurred; and record the pre-maximum pulse wave amplitude and the maximum pulse wave pressure in the recording unit.

3. The blood vessel training device according to claim 1, wherein the control module is configured to, in the pre-processing: control the pressure varying device so as to cause the pressure varying device to execute the first phase, which is processing including causing the pressure varying device to execute processing for decreasing the pressure of the gas inside the gas bladder so as to pass the range in which the pulse wave amplitude is expected to become maximum and then maintaining the pressure of the gas inside the gas bladder at a predetermined constant pressure during a period of 5 seconds to 15 seconds; perform processing for receiving the pulse wave data a plurality of times from the pulse wave measuring device while the pressure varying device is decreasing the pressure of the gas inside the gas bladder, to thereby identify a tentative pre-maximum pulse wave amplitude, which is a pulse wave amplitude that became maximum while the pressure varying device was decreasing the pressure of the gas inside the gas bladder, and the maximum pulse wave pressure, which is the pressure of the gas inside the gas bladder at a time at which the tentative pre-maximum pulse wave amplitude occurred; control the pressure varying device so that the predetermined constant pressure of the gas inside the gas bladder maintained during the period of 5 seconds to 15 seconds is the maximum pulse wave pressure; perform processing for receiving the pulse wave data a plurality of times from the pulse wave measuring device while the predetermined constant pressure of the gas inside the gas bladder is kept at the maximum pulse wave pressure, to thereby identify, as the pre-maximum pulse wave amplitude, the pulse wave amplitude that became maximum while the predetermined constant pressure of the gas inside the gas bladder was kept at the maximum pulse wave pressure; and record the identified pre-maximum pulse wave amplitude and the maximum pulse wave pressure in the recording unit.

4. The blood vessel training device according to claim 1, wherein the control module is configured to, in the treatment processing: determine, as the treatment pressure, a value obtained by multiplying the maximum pulse wave pressure recorded in the recording unit by 0.6 to 0.9; and control the pressure varying device so as to cause the pressure varying device to execute the second phase, which is processing for keeping the pressure of the gas inside the gas bladder at the treatment pressure.

5. The blood vessel training device according to claim 1, wherein the control module is configured to, in the treatment processing, control the pressure varying device so as to cause the pressure varying device to execute the second phase, which is processing for keeping the pressure of the gas inside the gas bladder constant throughout the predetermined time period between 1 minute and 15 minutes.

6. The blood vessel training device according to claim 1, wherein the control module is configured to, in the treatment processing, control the pressure varying device so as to cause the pressure varying device to execute the second phase, which is processing for alternately repeating a first time slot in which the pressure of the gas inside the gas bladder is equal to or smaller than the treatment pressure and equal to or larger than 30 mmHg and a second time slot in which the pressure of the gas inside the gas bladder is smaller than 30 mmHg, during the predetermined time period between 1 minute and 15 minutes, so that the first time slot per time ranges over a period between 15 seconds to 35 seconds and the second time slot per time ranges over a period between 15 seconds to 35 seconds.

7. The blood vessel training device according to claim 1, wherein the control module is configured to, in the post-processing: control the pressure varying device so as to cause the pressure varying device to execute the third phase, which is processing for keeping the pressure of the gas inside the gas bladder constant within a range equal to or larger than the maximum pulse wave pressure recorded in the recording unit and equal to or smaller than the pressure larger by 20 mmHg than the maximum pulse wave pressure during the period between the start point and the end point; perform processing for receiving the pulse wave data a plurality of times from the pulse wave measuring device while the third phase is being executed, to thereby identify the post-maximum pulse wave amplitude, which is the pulse wave amplitude that became maximum while the third phase was being executed; and record the post-maximum pulse wave amplitude in the recording unit.

8. The blood vessel training device according to claim 1, wherein the control module is configured to, in the post-processing: control the pressure varying device so as to cause the pressure varying device to execute the third phase, which is processing for linearly decreasing, during the period between the start point and the end point, the pressure of the gas inside the gas bladder from a range larger than the maximum pulse wave pressure recorded in the recording unit by 10 mmHg or larger and equal to or smaller than a pressure larger by 20 mmHg to a range of a pressure smaller than the maximum pulse wave pressure by at least 10 mmHg; perform processing for receiving the pulse wave data a plurality of times from the pulse wave measuring device while the third phase is being executed, to thereby identify the post-maximum pulse wave amplitude, which is the pulse wave amplitude that became maximum while the third phase was being executed; and record the post-maximum pulse wave amplitude in the recording unit.

9. The blood vessel training device according to claim 1, wherein the start point comprises a predetermined timing at which 40 seconds have not elapsed since 5 seconds elapsed from the end of the treatment processing.

10. The blood vessel training device according to claim 1, wherein the end point comprises a predetermined timing at which 200 seconds have not elapsed since 120 seconds elapsed from the end of the treatment processing.

11. The blood vessel training device according to claim 1, wherein the pulse wave measuring device is configured to measure, as the predetermined parameter, the pressure of the gas inside the gas bladder.

12. A blood vessel training system, comprising:
a tightener including:
    a belt having a length that allows the belt to be wrapped around a predetermined portion of any one of limbs of a subject;
    a fixing member configured to fix the belt under a state in which the belt is wrapped around the predetermined portion of the one of the limbs; and
    a gas bladder, which is provided to the belt, and is configured to apply a predetermined tightening pressure to the predetermined portion of the one of the limbs by tightening the predetermined portion of the one of the limbs through loading of a gas inside the gas bladder under a state in which the belt wrapped around the predetermined portion of the one of the limbs is fixed by the fixing member;

a pressure varying device configured to set a pressure of the gas inside the gas bladder to a desired pressure;

a pulse wave measuring device configured to measure, in a vicinity of a portion of the one of the limbs at which the tightener is fixed or on a further distal end side of the one of the limbs relative to the portion, a predetermined parameter varying in accordance with a variation of a magnitude of a pulse wave of an artery, and generate pulse wave data on a pulse wave amplitude based on the predetermined parameter;

a control module configured to receive the pulse wave data from the pulse wave measuring device and control the pressure varying device; and a recording unit configured to record data, wherein the control module is configured to execute:

pre-processing for: controlling the pressure varying device so as to cause the pressure varying device to execute a first phase, which is processing including at least changing the pressure of the gas inside the gas bladder so as to pass a range in which the pulse wave amplitude is expected to become maximum; performing at least processing for receiving the pulse wave data a plurality of times from the pulse wave measuring device while the first phase is being executed, to thereby identify a pre-maximum pulse wave amplitude, which is a pulse wave amplitude that became maximum while the first phase was being executed, and a maximum pulse wave pressure, which is the pressure of the gas inside the gas bladder at a time at which the pre-maximum pulse wave amplitude occurred; and recording the pre-maximum pulse wave amplitude and the maximum pulse wave pressure in the recording unit;

treatment processing for controlling the pressure varying device so as to cause the pressure varying device to execute a second phase, which is processing for executing a predetermined calculation operation on the maximum pulse wave pressure recorded in the recording unit to obtain a treatment pressure, which is a pressure smaller than the maximum pulse wave pressure, keeping the pressure of the gas inside the gas bladder during a predetermined time period between 1 minute and 15 minutes at such a ratio that a time period in which the pressure of the gas inside the gas bladder is equal to or smaller than the treatment pressure and equal to or larger than 30 mmHg is 50% or larger and a time period in which the pressure of the gas inside the gas bladder is smaller than 30 mmHg is 50% or smaller, and then decreasing the pressure of the gas inside the gas bladder to smaller than 30 mmHg, the treatment processing being executed subsequently to the pre-processing;

post-processing for: controlling the pressure varying device so as to cause the pressure varying device to execute a third phase, which is processing for changing the pressure of the gas inside the gas bladder within at least a range of +10 mmHg of the maximum pulse wave pressure recorded in the recording unit so as to pass the maximum pulse wave pressure, or keeping the pressure of the gas inside the gas bladder within a range equal to or larger than the maximum pulse wave pressure recorded in the recording unit and equal to or smaller than a pressure larger by 20 mmHg than the maximum pulse wave pressure recorded in the recording unit, during a period between a start point, which is a predetermined timing at which 45 seconds have not elapsed from an end of the treatment processing, and an end point, which is a predetermined timing at which at least 100 seconds have elapsed from the end of the treatment processing; performing processing for receiving the pulse wave data a plurality of times from the pulse wave measuring device while the third phase is being executed, to thereby identify a post-maximum pulse wave amplitude, which is a pulse wave amplitude that became maximum while the third phase was being executed; and recording the post-maximum pulse wave amplitude in the recording unit, the post-processing being executed subsequently to the treatment processing; and evaluation processing for evaluating a state of the blood vessel of the subject through use of the pre-maximum pulse wave amplitude and the post-maximum pulse wave amplitude that are recorded in the recording unit, the evaluation processing being executed after the post-processing.

13. A blood vessel training method to be executed by a control module of a blood vessel training device, the blood vessel training device being configured to form a blood vessel training system for increasing elasticity of a blood vessel in combination with:

a tightener including:

a belt having a length that allows the belt to be wrapped around a predetermined portion of any one of limbs of a subject;

a fixing member configured to fix the belt under a state in which the belt is wrapped around the predetermined portion of the one of the limbs; and a gas bladder, which is provided to the belt, and is configured to apply a predetermined tightening pressure to the predetermined portion of the one of the limbs by tightening the predetermined portion of the one of the limbs through loading of a gas inside the gas bladder under a state in which the belt wrapped around the predetermined portion of the one of the limbs is fixed by the fixing member;

a pressure varying device configured to set a pressure of the gas inside the gas bladder to a desired pressure; and a pulse wave measuring device configured to measure, in a vicinity of a portion of the one of the limbs at which the tightener is fixed or on a further distal end side of the one of the limbs relative to the portion, a predetermined parameter varying in accordance with a variation of a magnitude of a pulse wave of an artery, and generate pulse wave data on a pulse wave amplitude based on the predetermined parameter, the blood vessel training device including:

the control module configured to receive the pulse wave data from the pulse wave measuring device and control the pressure varying device; and a recording unit configured to record data, the blood vessel training method comprising executing, by the control module:

pre-processing for: controlling the pressure varying device so as to cause the pressure varying device to execute a first phase, which is processing including at least changing the pressure of the gas inside the gas bladder so as to pass a range in which the pulse wave amplitude is expected to become maximum; performing at least processing for receiving the pulse wave data a plurality of times from the pulse wave measuring device while the first phase is being executed, to thereby identify a pre-maximum pulse wave amplitude, which is a pulse wave amplitude that became maximum while the first phase was being executed, and a maximum pulse wave pressure, which is the pressure of the gas inside the gas bladder at a time at which the pre-maximum pulse wave amplitude occurred; and recording the pre-maximum pulse wave amplitude and the maximum pulse wave pressure in the recording unit;

treatment processing for controlling the pressure varying device so as to cause the pressure varying device to execute a second phase, which is processing for executing a predetermined calculation operation on the maximum pulse wave pressure recorded in the recording unit to obtain a treatment pressure, which is a pressure smaller than the maximum pulse wave pressure, keeping the pressure of the gas inside the gas bladder during a predetermined time period between 1 minute and 15 minutes at such a ratio that a time period in which the pressure of the gas inside the gas bladder is equal to or smaller than the treatment pressure and equal to or larger than 30 mmHg is 50% or larger and a time period in which the pressure of the gas inside the gas bladder is smaller than 30 mmHg is 50% or smaller, and then decreasing the pressure of the gas inside the gas bladder to smaller than 30 mmHg, the treatment processing being executed subsequently to the pre-processing;

post-processing for: controlling the pressure varying device so as to cause the pressure varying device to execute a third phase, which is processing for changing the pressure of the gas inside the gas bladder within at least a range of +10 mmHg of the maximum pulse wave pressure recorded in the recording unit so as to pass the maximum pulse wave pressure, or keeping the pressure of the gas inside the gas bladder within a range equal to or larger than the maximum pulse wave pressure recorded in the recording unit and equal to or smaller than a pressure larger by 20 mmHg than the maximum pulse wave pressure recorded in the recording unit, during a period between a start point, which is a predetermined timing at which 45 seconds have not elapsed from an end of the treatment processing, and an end point, which is a predetermined timing at which at least 100 seconds have elapsed from the end of the treatment processing; performing processing for receiving the pulse wave data a plurality of times from the pulse wave measuring device while the third phase is being executed, to thereby identify a post-maximum pulse wave amplitude, which is a pulse wave amplitude that became maximum while the third phase was being executed; and recording the post-maximum pulse wave amplitude in the recording unit, the post-processing being executed subsequently to the treatment processing; and evaluation processing for evaluating a state of the blood vessel of the subject through use of the pre-maximum pulse wave amplitude and the post-maximum pulse wave amplitude that are recorded in the recording unit, the evaluation processing being executed after the post-processing.

\* \* \* \* \*